US012609195B2

(12) United States Patent
Buschle et al.

(10) Patent No.: US 12,609,195 B2
(45) Date of Patent: Apr. 21, 2026

(54) MEDICAL IMAGING DEVICE, MEDICAL SYSTEM, METHOD FOR OPERATING A MEDICAL IMAGING DEVICE, AND METHOD FOR MEDICAL IMAGING

(71) Applicant: KARL STORZ SE & Co. KG, Tuttlingen (DE)

(72) Inventors: Lukas Buschle, Tuttlingen (DE); Johannes Fallert, Tuttlingen (DE); Werner Göbel, Tuttlingen (DE); Klaus Hammerl, Tuttlingen (DE); Sebastian Wagner, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 18/839,946

(22) PCT Filed: Feb. 20, 2023

(86) PCT No.: PCT/EP2023/054223
§ 371 (c)(1),
(2) Date: Aug. 20, 2024

(87) PCT Pub. No.: WO2023/161193
PCT Pub. Date: Aug. 31, 2023

(65) Prior Publication Data
US 2025/0166796 A1      May 22, 2025

(30) Foreign Application Priority Data
Feb. 22, 2022      (DE) ..................... 10 2022 104 138.7

(51) Int. Cl.
*G16H 30/40*      (2018.01)
(52) U.S. Cl.
CPC .................................. *G16H 30/40* (2018.01)

(58) Field of Classification Search
CPC ...... G16H 30/40; A61B 5/0075; A61B 5/4836
See application file for complete search history.

(56) References Cited

U.S. PATENT DOCUMENTS

2010/0168562 A1      7/2010  Zhao et al.
2013/0296709 A1*     11/2013 Zuzak ................... G01J 3/0208
                                                      600/476
(Continued)

FOREIGN PATENT DOCUMENTS

DE      112020003749 T5      2/2021
DE      102020105458 A1      6/2021
(Continued)

OTHER PUBLICATIONS

M. J. Khan et al.: Modern Trends in Hyperspectral Image Analysis: Review; IEEE Access, 6 (2018), pp. 14118-14129 (Year: 2018).*
(Continued)

*Primary Examiner* — Joshua B Blanchette
(74) *Attorney, Agent, or Firm* — Jason H. Vick; Amped IP LLC

(57)      ABSTRACT
The invention relates to a medical imaging device (10), comprising: a spatially and spectrally resolving image acquisition unit (12) which comprises at least one optical system (14) and at least one image acquisition sensor system (16) coupled to the optical system (14), which are configured to generate image data of an object region (18) which comprise spatial and spectral information; an image analysis unit (20) which is configured to create an analysis of the image data which is based on spatial and spectral information, wherein the analysis comprises at least one evaluation which comprises at least one evaluation parameter which relates to an object subregion (22) of the object region (18); an assessment unit (24) which is configured to generate, based on the analysis and on the basis of information relating to a diagnostic and/or therapeutic activity that is to be carried out
(Continued)

and/or has been carried out, an assessment of an attribute of the object subregion (22) relevant to the diagnostic and/or therapeutic activity, which assessment is based on the evaluation parameter; and an output generation unit (26) which is configured to generate an output that is based on the assessment.

The invention also relates to a medical system (56) with a medical imaging device (10) as well as associated methods.

15 Claims, 9 Drawing Sheets

(56) References Cited

U.S. PATENT DOCUMENTS

| | | | |
|---|---|---|---|
| 2016/0069743 A1* | 3/2016 | McQuilkin | A22B 5/007 356/416 |
| 2016/0239967 A1* | 8/2016 | Chou | G06T 7/11 |

| | | | |
|---|---|---|---|
| 2017/0150923 A1 | 6/2017 | Bonfils-Rasmussen | |
| 2018/0116526 A1* | 5/2018 | Panasyuk | A61B 5/4842 |
| 2020/0304753 A1 | 9/2020 | Venkataraman et al. | |
| 2021/0196425 A1 | 7/2021 | Shelton, IV et al. | |
| 2021/0199557 A1 | 7/2021 | Shelton, IV et al. | |
| 2021/0216822 A1 | 7/2021 | Paik et al. | |
| 2021/0306542 A1* | 9/2021 | Kulcke | H04N 5/77 |

FOREIGN PATENT DOCUMENTS

| | | |
|---|---|---|
| WO | WO 2017/057030 A1 | 4/2017 |
| WO | WO 2020/194942 A1 | 1/2020 |

OTHER PUBLICATIONS

International Search Report for International Patent Application No. PCT/EP2023/054223, mailed Oct. 20, 2023.

Written Opinion for International Patent Application No. PCT/EP2023/054223, mailed Oct. 20, 2023.

* cited by examiner

MEDICAL IMAGING DEVICE, MEDICAL SYSTEM, METHOD FOR OPERATING A MEDICAL IMAGING DEVICE, AND METHOD FOR MEDICAL IMAGING

CROSS-REFERENCE TO RELATED APPLICATIONS

This application is a national stage application under 35 U.S.C. 371 of PCT Application No. PCT/EP2023/054223 having an international filing date of 20 Feb. 2023, which designated the United States, which PCT application claimed the benefit of German Application No. 10 2022 104 138.7, filed 22 Feb. 2022, each of which are incorporated herein by reference in their entirety.

SUMMARY

The invention relates to a medical imaging device, a medical system, a method for operating a medical imaging device, and a method for medical imaging.

Medical imaging devices, such as endoscopic devices that operate multispectrally or hyperspectrally, are known from the prior art. An object to be imaged, such as a site for a minimally invasive intervention, is acquired with spectral resolution so that individual spectral information is obtained for each of the different acquired pixels. From DE 10 2020 105 458 A1, for example, an imaging device is known which has an adjustable spectral filter that allows images to be taken in different spectral ranges in order to generate multispectral image data.

In principle, multispectral or hyperspectral image data can be obtained using different methods. In the so-called whiskbroom approach, the object to be imaged is scanned point by point, wherein a spectrum is obtained for each point. In the so-called pushbroom method, a complete image line is recorded at a time. By using a two-dimensional detector, a spectrum can then be recorded for each point in the image line. In addition, it is also possible to record a plurality of images sequentially through different spectral filters in a so-called staring approach. Each individual recorded image contains complete spatial information for a single spectral range. Furthermore, there are approaches to break down a two-dimensional multi-color image into a plurality of individual spectral images using suitable optical elements, such as optical slicers, lenses and prisms, which are simultaneously acquired on different detectors or detector regions. This is sometimes referred to as the snapshot approach.

Imaging methods are of central importance in the medical field, in particular in connection with minimally invasive surgical methods, but also generally for diagnostics and for assessing the success or quality of an intervention. For example, a site can be observed during a minimally invasive intervention when tissue is to be or has been fused, for example using an electrosurgical device, such as a high-frequency coagulation instrument. Other examples of diagnostic and/or therapeutic activities before, during or after which observation by means of imaging methods is appropriate are the observation and assessment of ligatures, clips and stapler inserts, tissue sampling or generally various surgical interventions.

The invention is in particular based on the object of providing an imaging device and an imaging method by means of which the safety, quality and/or efficiency of diagnostic and/or therapeutic activities can be increased.

This object is achieved according to the invention by the features of the independent claims. Further developments of the invention can be found in the dependent claims.

An imaging device according to the invention can comprise a spatially and spectrally resolving image acquisition unit which comprises at least one optical system and at least one image acquisition sensor system coupled to the optical system, which are configured to generate image data of an object region which comprise spatial and spectral information. Furthermore, the imaging device can comprise an image analysis unit which is configured to create an analysis of the image data that is based on spatial and spectral information, wherein the analysis comprises at least one evaluation which comprises at least one evaluation parameter which relates to an object subregion of the object region. In addition, the imaging device can comprise an assessment unit which is configured, based on the analysis and on the basis of information relating to a diagnostic and/or therapeutic activity that is to be carried out and/or has been carried out, to generate an assessment of an attribute of the object subregion relevant to the diagnostic and/or therapeutic activity, which assessment is based on the evaluation parameter. Furthermore, the imaging device can comprise an output generating unit that is configured to generate an output which is based on the assessment.

According to one aspect, a medical system is provided that comprises the imaging device and a medical device.

One aspect also relates to a method for operating a medical imaging device that comprises a spatially and spectrally resolving image acquisition unit that comprises at least one optical system and at least one image acquisition sensor system coupled to the optical system, which are configured to generate image data of an object region that comprise spatial and spectral information. This can be an imaging device according to the invention. The method can comprise a step of at least partially automated, in particular automated, generation/acquisition of image data of the object region, which comprise spatial and spectral information. The method can comprise a step of at least partially automated, in particular automated, creation of an analysis of the image data that is based on spatial and spectral information, wherein the analysis comprises at least one evaluation which comprises at least one evaluation parameter which relates to an object subregion of the object region. The method can also comprise at least partially automated, in particular automated, generation, based on the analysis and on the basis of information relating to a diagnostic and/or therapeutic activity that is to be carried out and/or has been carried out, of an assessment of an attribute of the object subregion relevant to the diagnostic and/or therapeutic activity, which assessment is based on the evaluation parameter. The method can also comprise at least partially automated, in particular automated, output of an output that is based on the assessment.

Furthermore, one aspect relates to a method for medical imaging. The method can be carried out with an imaging device according to the invention and/or with a medical system according to the invention. The method can comprise a step of at least partially automated, in particular automated, generation/acquisition of image data of the object region, which comprise spatial and spectral information. The method can comprise a step of at least partially automated, in particular automated, creation of an analysis of the image data that is based on spatial and spectral information, wherein the analysis comprises at least one evaluation which comprises at least one evaluation parameter which relates to an object subregion of the object region. The method can also comprise at least partially automated, in particular automated, generation, based on the analysis and on the basis of information relating to a diagnostic and/or therapeutic activity that is to be carried out and/or has been carried out, of an assessment of an attribute of the object subregion relevant to the diagnostic and/or therapeutic activity, which assessment is based on the evaluation parameter. The method can also comprise at least partially automated, in particular automated, output of an output that is based on the assessment.

These features make it possible to achieve a high degree of safety in the planning, implementation and/or assessment of diagnostic and/or therapeutic activities. Furthermore, a high degree of quality can be achieved. Furthermore, the efficiency in the planning, implementing, assessing and/or in the training of such diagnostic and/or therapeutic activities can be increased. By at least partially automated generation and output of an assessment based on an analysis of image data, a user can be supported in a targeted and effective manner. Even users with comparatively little experience can be shown options for diagnostic and/or therapeutic activities for therapy and/or diagnosis or can be supported and guided in this, which can optimize the result for the patient.

The imaging device can be a microscopic, macroscopic and/or exoscopic imaging device. The imaging device can be configured as a microscope, macroscope and/or exoscope and/or comprise such. In some embodiments, the imaging device is an endoscopic imaging device. The imaging device can be an endoscope device. It can comprise an endoscope and/or an endoscope system and/or be configured as such and/or form at least a part and preferably at least a major part and/or main component of an endoscope and/or an endoscope system. "At least a major part" can mean at least 55%, preferably at least 65%, more preferably at least 75%, particularly preferably at least 85% and most preferably at least 95%, in particular with reference to a volume and/or a mass of an object.

In some embodiments, the imaging device is configured to be insertable into a cavity for inspection and/or observation, for example into an artificial and/or natural cavity, such as into the interior of a body, into a body organ, into tissue or the like. The imaging device can also be configured to be insertable into a housing, casing, shaft, tube or other, in particular artificial, structure for inspection and/or observation.

The imaging device and in particular the optical system and/or the image acquisition sensor system can be configured for multispectral and/or hyperspectral imaging, in particular for acquiring and/or generating multispectral and/or hyperspectral image data. Multispectral imaging or multispectral image data can refer in particular to such imaging in which at least three spectral bands can be acquired and/or are acquired independently of one another. Hyperspectral imaging or hyperspectral image data can refer in particular to imaging in which at least 20, at least 50 or even at least 100 spectral bands can be acquired and/or are acquired independently of one another. The imaging device can operate according to the pushbroom principle, and/or the whisk-broom principle, and/or the staring principle, and/or a snap-shot principle.

In some embodiments, the imaging device comprises a white light camera and/or sensor system for white light imaging. The imaging device can be configured for white light imaging in addition to spectrally resolved imaging. A separate optical system and/or a common optical system can be used for this purpose. White light imaging and spectrally resolved imaging can be performed simultaneously or alternately, or sometimes simultaneously and sometimes sequentially.

For some applications it can be advantageous to be able to use a high spectral resolution. Hyperspectral imaging is then recommended. This can be combined with white light imaging. This makes real-time observation possible via a white light image, even if the acquisition of spectrally resolved image data only occurs substantially in real time, i.e., for example, several seconds are needed to create a spectrally resolved image.

For some applications it can be advantageous to generate spectral image data in real time. This includes, for example, the generation of a spectrally resolved image in less than a second or even several times per second. It can be useful to use multispectral imaging in this case. An optionally lower spectral resolution is then offset by a higher refresh rate. Depending on the application, it can be sufficient to consider only a few different spectral ranges and/or wavelengths, for example two or three or four or generally less than ten. In this case, additional white light imaging can optionally be omitted. Spectrally resolved image data that are acquired in real time or deliver several images per second can also be used for monitoring purposes, wherein it is not absolutely necessary to create a reproducible image for a user, but rather the image data can also be processed in the background.

The medical imaging device can have at least a proximal portion, a distal portion and/or an intermediate portion. The distal portion is in particular configured to be introduced into and/or located in a cavity to be examined in an operating state, for example during the diagnostic and/or therapeutic activity. The proximal portion is in particular configured to be arranged outside the cavity to be examined in an operating state, for example during the diagnostic and/or therapeutic activity. "Distal" should be understood to mean, in particular, facing a patient and/or facing away from a user during use. "Proximal" should be understood to mean, in particular, facing away from a patient and/or facing a user during use. In particular, proximal is the opposite of distal. The medical imaging device in particular has at least one, preferably flexible, shaft. The shaft can be an elongated object. Furthermore, the shaft can at least partially and preferably, at least to a large extent, form the distal portion. An "elongated object" is to be understood in particular as an object whose main extension is at least a factor of five, preferably at least a factor of ten and particularly preferably at least a factor of twenty larger than a largest extension of the object perpendicular to its main extension, i.e. in particular a diameter of the object. A "main extension" of an object should be understood in particular as its longest extension along its main extension direction. A "main extension direction" of a component is to be understood in particular as a direction which runs parallel to a longest edge of a smallest imaginary cuboid which only just completely encloses the component.

The image acquisition unit can be arranged at least partially and preferably at least to a large extent in the region of the proximal portion and/or can form it. In other embodiments, the image acquisition unit can be arranged at least partially and preferably at least to a large extent in the distal portion and/or can form it. Furthermore, the image acquisition unit can be arranged at least partially distributed over the proximal portion and the distal portion. The image acquisition sensor system comprises in particular at least one image sensor. Furthermore, the image acquisition sensor system can also have at least two and preferably several image sensors, which can be arranged one behind the other. Furthermore, the two and preferably several image acquisition sensors can have spectral acquisition sensitivities different from one another so that, for example, a first sensor in a red spectral range, a second sensor in a blue spectral range and a third sensor in a green spectral range is particularly sensitive or comparatively more sensitive than the other sensors. The image sensor can be configured as a CCD sensor and/or a CMOS sensor.

The optical system of the image acquisition unit can comprise suitable optical elements, such as lenses, mirrors, gratings, prisms, optical fibers, etc. The optical system can be configured to guide object light coming from the object region to the image acquisition sensor system, for example to focus and/or project it. The object light can in particular come from illumination of the object region.

The image acquisition unit is in particular configured to generate at least two-dimensional spatial image data. The image acquisition unit can be spatially resolving in such a way that it provides a resolution of at least 100 pixels, preferably of at least 200 pixels, preferably of at least 300 pixels and advantageously of at least 400 pixels in at least two different spatial directions. The image data are preferably at least three-dimensional, wherein at least two dimensions are spatial dimensions and/or wherein at least one dimension is a spectral dimension. From the image data, several spatially resolved images of the object region can be obtained, each of which is assigned to different spectral bands. The spatial and spectral information of the image data can be such that an associated spectrum can be obtained for a plurality of spatial pixels.

In some embodiments, the image acquisition unit is configured to generate continuously updated image data. The image acquisition unit can, for example, be configured to generate the image data substantially in real time, which can comprise, for example, generating updated image data at least every 30 seconds, in some cases at least every 20 seconds, and in some cases even at least every 10 seconds or at least every 5 seconds.

The object region can be an image region comprising at least a part and/or portion of an imaged object. The object region can concern tissues and/or organs and/or a part of a body of a patient. For example, the object can be a site. The object region can concern a site.

The imaging device can comprise a lighting device that comprises at least one illuminant which is configured to light up and/or illuminate the object region in at least one operating state. The illuminant can comprise a white light source, a, in particular tunable, monochrome light source, a laser, a white light laser, at least one light-emitting diode and/or a light-emitting diode array, at least one laser diode and/or a laser diode array or the like. The lighting device can be formed integrally with the image acquisition unit. In particular, the lighting device can use individual or all components of the optical system of the image acquisition unit and/or have a separate lighting optical system. An illumination light beam can be guided and/or guidable at least in portions coaxially with a measuring light beam.

The analysis of the image data is based in particular on both spatial and spectral information. The evaluation can be based on processing both spatial and spectral information to determine the evaluation parameter. The object subregion can be selected at least partially automatically and in particular automatically. Alternatively or additionally, the object subregion can be selected and/or defined by a user. For example, it can be provided that the user selects the object subregion by clicking, drawing, marking out, tapping or the like, for example starting from a representation of the object region. The evaluation parameter can be obtained in particular from spectral information assigned to the object subregion by means of a mathematical rule. In particular, the evaluation parameter can assume a continuous value range of 0-100% or a discrete value range of 0.1, 2, . . . . The mathematical rule can comprise an algebraic calculation rule and/or a machine learning method, e.g. an AI model. The evaluation parameter is based in particular on a spectral value for a specific wavelength, and/or a specific wavelength range, and/or a specific spectral band.

The diagnostic and/or therapeutic activity that is to be carried out and/or has been carried out can be planned, and/or is currently being carried out, and/or is already partially or fully completed. The diagnostic and/or therapeutic activity can comprise at least one diagnostic step and/or treatment step and/or therapy step. The diagnostic and/or therapeutic activity can alternatively or additionally be in relation to the startup, maintenance and/or adjustment of a medical device and/or the imaging device itself. For example, it can be sterilization and/or cleaning, such as at least partially automated or automatic cleaning of a window, such as a distal end window and/or illumination window, of the imaging device. In some embodiments, the diagnostic and/or therapeutic activity is a diagnosis and/or an intervention and/or a treatment. The diagnostic and/or therapeutic activity can be invasive and/or microinvasive. For example, the diagnostic and/or therapeutic activity can be vessel sealing, tubal sterilization, fusing and/or connecting of tissue structures, such as anastomosis formation, ligation, insufflation, gas humidification, application of clips, suturing or stapling, cutting open certain structures, such as vascular structures, bile ducts, nerve fibers, lymph nodes/pathways, fascia, etc., removal of concretions, such as kidney stones, gallstones, etc., tissue denaturation, suctioning of secretions, treatment of stenoses or the like.

The information, hereinafter also referred to as "assessment information", which underlies the assessment in addition to the analysis, is different in particular from the spatial and spectral information. The assessment information can be such that it cannot be obtained from the spatial and spectral information. The assessment is based in particular on the evaluation and additionally includes consideration of the specific circumstances when planning, carrying out or evaluating the diagnostic and/or therapeutic activity. The mentioned specific circumstances can also arise from prior knowledge, for example, that is obtained from device parameters and/or AI detection in the white light image and/or preoperative imaging. The assessment information can be present in a database and/or originate from artificial intelligence or be obtained from a neural network. The assessment information can be based on empirical values and/or previous results and can comprise, for example, lookup tables, value ranges, thresholds, categorical data, image data, spectral data, etc. that are associated with a particular diagnostic and/or therapeutic activity. In some embodiments, the assessment information is alternatively or additionally associated with the status of the diagnostic and/or therapeutic activity, in particular whether the activity is planned and/or is currently being performed and/or has been performed.

In some embodiments, the relevant attribute relates to a suitability and/or unsuitability of the object subregion for the diagnostic and/or therapeutic activity that is to be performed and/or has been performed. The attribute can alternatively or additionally relate to a quality and/or a condition of the object subregion, or the object and/or treatment result depicted therein. The attribute can be categorical, and/or metric, and/or numeric.

The output is, in some embodiments, a digital output and/or an analog output. The output can be directed to a user and/or a device or can comprise information that is processable by a user and/or a device.

The imaging device can comprise a control unit. The control unit can comprise suitable control electronics and/or a computer. In some embodiments, the control unit comprises at least a processor, computer-readable memory, an operating system, and/or suitable inputs and outputs. The control unit contains at least one control program. The image acquisition unit, the image analysis unit, the assessment unit and/or the output generation unit can be at least partially formed by the control unit. In particular, functions thereof can be implemented by the control program or be part thereof. The imaging device and in particular the control unit can in each case comprise at least one processor and/or an associated memory with program code that implements the described functions and steps, and/or an associated random access memory, and/or associated ports, and/or data interfaces, and/or an electronic circuit in order to implement the functional units mentioned herein and/or to carry out the method steps mentioned herein. One or more processors, memories, main memories, connections, data interfaces and/or circuits can also be assigned to one or more functional units and/or implement one or more method steps.

The imaging device can comprise an output unit that is configured to output the output, and/or user output generated in accordance with the output to a user. The output unit can be configured to output a visual output, and/or an audio output, and/or a haptic output, and/or any other output perceptible by a user. For this purpose, the output unit can comprise suitable components, such as one or more lamps, illuminants, loudspeakers, screens, vibrators or the like. The output unit can comprise a computer and/or processor, and/or memory, and/or random access memory, and/or ports, and/or a data interface for receiving, processing and outputting unprocessed, preprocessed and/or processed output data. The output generation unit can be connected to the output unit via an interface. The generated output can be processed and/or output by the output unit.

The imaging device can comprise a display unit that is configured to display an image, in particular a moving image, to a user. The display unit can be part of the output unit and/or form it. The displayed image can be based on the image data. The display unit can comprise a screen and/or control electronics. The display unit can comprise a computer and/or processor, and/or memory, and/or random access memory, and/or ports, and/or a data interface for receiving, processing and outputting unprocessed, preprocessed and/or processed image data and/or display data. The output generation unit can be connected to the display unit via an interface. The generated output can be processed and/or output by the display unit.

The imaging device can comprise an audio output unit that is configured to output an audio signal. The audio output unit can be part of the output unit and/or form it. The audio output unit can comprise a loudspeaker and/or control electronics. The audio output unit can comprise a computer and/or processor, and/or memory, and/or random access memory, and/or ports, and/or a data interface for receiving, processing and outputting unprocessed, preprocessed and/or processed output data. The output generation unit can be connected to the audio output unit via an interface. The generated output can be processed and/or output by the audio output unit.

The imaging device can comprise a user interface configured to enable a user to make an input. Such input can be for operating the imaging device, and/or for operating the medical device, and/or for operating the display unit. The user interface can comprise input means, such as buttons, rotary switches, a touch display, a mouse, a keyboard, a voice input, at least one foot switch or the like.

The output unit, and/or the audio output unit, and/or the display unit, and/or the user interface can be integrated.

The imaging device can comprise an imaging unit. The imaging unit can, for example, be an endoscope. The imaging unit can at least partially comprise the imaging unit, in particular at least the optical and/or sensory components of the imaging unit.

The imaging device can comprise a lighting device. The lighting device can comprise at least part of the lighting unit, in particular at least its electronic and/or optical components.

The imaging device can comprise an output device. The output device can comprise at least a part of the output unit, in particular at least a part of the display unit and/or the audio output unit, for example its electronic and/or mechanical components, such as a screen, a loudspeaker, etc.

The imaging device can comprise a control unit. The control unit can comprise the control unit at least partially or completely, in particular its electronic components.

User interface components can be distributed across different devices or all arranged in one of the devices.

The imaging unit can be connected to the lighting device via an electronic and/or optical interface. The imaging unit, and/or the lighting device, and/or the output device can be connected to the control unit via a preferably electronic and/or optical interface.

The mentioned methods can each be carried out in particular within the framework of a simulation, and/or demonstration, and/or during a test, and/or a trial run away from the patient. The diagnostic and/or therapeutic activity that is to be performed and/or has been performed can be real and/or virtual. In particular, the implementation of this activity is not part of the abovementioned procedures. The above-mentioned procedures can each be carried out with the aid of a computer. For example, one or more of the at least partially automated steps can comprise calculations that at least one processor performs and/or that are based on the execution of program code.

The medical device can be an in particular diagnostic, and/or therapeutic and/or surgical device, and/or instrument and/or tool, etc. In some embodiments, the medical device is a laparoscopic instrument. For example, the medical device can comprise and/or form an insufflator, a light source, an anesthesia device, an energetic system and/or an energetic device, such as an RF instrument, a laser instrument, a motorized instrument, a medical robot, an endoscope, an endoscope system, a suturing device or a suturing system, a light source or a lighting system or the like. The medical device can be arranged at least partially in the object region before, during and/or after the diagnostic and/or therapeutic activity. The imaging is then used, among other things, to observe the medical device, for example a tool thereof, before, during and/or after the impact on body parts in the object region.

In some embodiments, the medical device is a tissue-coagulating, in particular vessel-sealing or tissue-welding, instrument. The medical device can be configured to specifically deliver energy into tissue. The medical device can comprise an RF generator. Alternatively or additionally, the medical device can comprise a laser, a radiation source and/or another energy source. An energy output of the medical device can be adjustable, in particular with regard to an energy amount, a power, a temporal and/or spatial output profile, an output frequency, an output waveform, or the like.

A connection between the imaging device and the medical device can be easily established in particular if the medical imaging device comprises a device interface to which the medical device can be and/or is connected, in particular detachably and/or without tools. The device interface can be wired and/or wireless. The device interface can be configured to connect to different medical devices, for example selectively or simultaneously. The imaging device can have a device detection unit that automatically detects the kind, and/or type, and/or model of the medical device. The detection can be taken into account for the assessment. For example, the relevant attribute can depend on the nature, and/or type, and/or model of the detected medical device.

According to one aspect, the imaging device comprises a recommendation unit that is configured to generate a recommendation for a user based on the assessment of the attribute of the object subregion. The output generation unit can be configured to generate the output based on the recommendation. By generating a recommendation, a user can be supported in being able to provide a more accurate situational assessment. For example, a user can thereby indirectly draw on the experience of other clinicians, testers, surgeons, diagnosticians, etc. because their experience is reflected in the recommendation.

The recommendation can be a recommended action for carrying out a diagnostic and/or therapeutic activity on a patient. This can comprise a suggestion to perform a particular activity, to select one of several activities, not to perform a particular activity and/or a series of particular activities, to perform activities in a particular order or not, and the like. The recommended action can be categorical, in particular nominally scaled. The recommended action can also be ordinally scaled. In some embodiments, the recommended action can comprise multiple alternatives, which can in particular be sorted according to a recommended ranking. By using a recommended action, a user can be encouraged to perform a diagnosis and/or treatment in a certain way, thereby achieving a high degree of efficiency in planning and implementation. In addition, the associated prospects of success can be increased or the risk of errors minimized because, depending on the result of the assessment, a recommendation adapted to the situation can be generated.

A user can be supported effectively and in a targeted manner, in particular if the recommendation concerns the selection, and/or setting, and/or handling of a medical device other than the imaging device. For example, the recommendation unit can be configured to suggest to the user, on the basis of the assessment of the attribute, which therapeutic and/or diagnostic activity appears to be medically appropriate and to suggest suitable equipment, a suitable methodology and/or a suitable configuration for this purpose.

In some embodiments, the recommendation relates to whether and/or in which region the object region should be surgically acted on. Alternatively or additionally, the recommendation relates to whether and/or in which region of the object region there should be no surgical intervention. This can make it easier for a user to quickly and reliably identify medically relevant tissue structures, organs, body parts, tissue portions, etc., can guide him to work in a region that promises informative diagnostics and/or treatment success, and can prevent him from working in a region that could result in inadequate diagnosis and/or unsuccessful treatment.

The recommendation can be generated very precisely and/or adequately if it is based on a comparison of the assessment with a database. The database can contain data records of different diagnostic and/or therapeutic activities that are to be performed and/or have been performed, as well as, in some embodiments, associated recommendations. The recommendation can be based on the selection of a specific data acquired from the database which operates according to a best-match algorithm. In some embodiments, the recommendation can also be based on a combination of multiple data records. The recommendation can therefore go beyond the diagnostic and/or therapeutic situations that are contained in the database. In particular, the recommendation can be determined in a multi-stage process in which a first partial assessment is initially used to recommend a specific diagnostic and/or therapeutic activity and in which, based on the selected diagnostic and/or therapeutic activity and a second partial assessment for this activity, situation-appropriate settings, handling recommendations for an employed medical device, recommendations regarding suitable and/or unsuitable regions of the body region under consideration, etc. are recommended. Furthermore, it can be provided that the assessment is carried out in several stages. In particular, an initial database comparison can be carried out based on an initial partial assessment. The result of the first database comparison can be used as the basis for a second partial assessment. The second partial assessment can in turn be used for a second database comparison. In this way, the recommendation can be generated step by step and based on combinations of data records that are not explicitly saved in the database itself.

A high degree of certainty can be achieved in particular if the assessment comprises the detection and/or classification of risk structures. The recommendation can comprise information regarding the detection and/or classification of risk structures. This can also reduce the likelihood of treatment errors. In particular, a subregion of the object region that is not to be therapeutically influenced, in particular not with a medical device that is currently in use and/or connected to the imaging device, can be detected as a risk structure. The risk structure can, for example, be a region in which no incision and/or tissue coagulation should be performed, for example due to fear of bleeding. Depending on the type of diagnostic and/or therapeutic activity, risk structures can be different body parts, tissue types, vessels, organs, regions, etc., specifically those that a competent user and/or doctor and/or clinician would identify as unsuitable for the activity if he had detected it. The classification can be two-stage, such as "suitable" and "unsuitable", but also multi-stage, in particular at least three-stage.

According to one aspect, the imaging device comprises an evaluation unit that is configured to assign at least one evaluation to the recommendation in response to a behavior of the user caused by the recommendation. By accordingly taking into account how a user behaved and whether or not, for example, a recommended action was followed, the quality of the recommendation can be assessed. The evaluation unit can also be configured to transmit the evaluation to a recommendation database. This can provide a learning system that can utilize human input to generate future recommendations of higher quality. The recommendation database can be part of the mentioned database or different therefrom. The behavior of the user can be an acceptance, and/or rejection, and/or adaptation of a recommended action.

Supporting the user during a diagnosis, an intervention and/or a treatment can be in particular very effective if the recommendation unit is configured to adapt the recommendation substantially in real time depending on continuously updated image data. For example, an updated recommendation can be determined for updated image data in each case. This allows the recommendation to be adjusted if a viewing angle and/or image portion changes, if the site changes, if the medical device is moved and/or modified, etc.

According to one aspect, the imaging device comprises a parameter determination unit which is configured to determine at least one control parameter for controlling a medical device on the basis of the assessment of the attribute of the object subregion. The output generating unit can be configured to generate the output based on the at least one control parameter. By determining a control parameter, a medical device in use can be employed very effectively. A user can be supported in using suitable parameters appropriate to the situation. This means that even a less experienced user can employ the medical device without personally having to know all the details regarding its optimal setting. The control parameter can relate to a flow rate and/or a gas composition of a gas humidifying insufflator, brightness and/or spectral settings of a light source, a delivery rate of an anesthesia machine, parameters for setting a robot, such as position, orientation, feed rate, gripping force, etc., optical setting parameters, such as focus, aperture, exposure time, color contrast enhancements in the parallel white light video, etc., a shape and/or size of a needle in use, a thread material, a closing force for a stapler, cleaning parameters for cleaning a window, or the like.

The control parameter can be read from at least one list, table, database or the like. Alternatively or additionally, the control parameter can be calculated by a machine learning algorithm, such as based on an RNN model, an LSTM model, according to a random forest method or the like.

If the imaging device comprises a device interface, this can be configured to transmit the at least one control parameter to the medical device. This allows suitable parameters to be transferred to the medical device in an efficient manner. Instead of manual input or using a program or a parameter set that is saved in the medical device regardless of the situation, a parameter set adapted to the individual diagnosis or therapy situation can accordingly be used.

In some embodiments, the control parameter can be transmitted to the medical device automatically and/or without user input, in particular at least substantially in real time. For this purpose, it can be provided that the parameter determination unit and the output generation unit can operate in an automatic mode, in particular selectively activatable by the user. This can ensure that optimized parameters are used reliably.

Alternatively or additionally, the output can comprise a suggestion for a user to automatically pass on the at least one control parameter to a medical device that can be controlled by means of the control parameter. This can relieve the user and allow the focus to be directed more to the diagnostic and/or therapeutic activity rather than to adjusting the medical device. The suggestion can, for example, comprise a set of parameters. In this way, various settings on the medical device can be made automatically through a simple approval by the user. At the same time, it is ensured that no settings are made without user approval.

The user interface can be configured to receive at least one user input by means of which the user can accept, and/or reject, and/or adapt the suggestion. In a simple and intuitively understandable way, the user can be brought to the level of a very experienced doctor or clinician by suitable control parameters being suggested to him. Nevertheless, the decision as to whether and in what manner the medical device should actually be controlled can remain with the user. Furthermore, this can enable the user to make adjustments that he considers necessary based on his individual assessment. The suggestion can comprise a display of a parameter set, a graphical representation, an overlay, especially in data glasses, an audio description of the settings to be made or the like.

Situationally adapted and therefore optimized settings of the medical device can in particular be provided reliably and effectively if the parameter determination unit is configured to adapt the at least one control parameter substantially in real time depending on continuously updated image data. In some embodiments, it can be provided that the output can comprise an overlay and/or display and/or representation of a current control parameter or parameter set by means of which the user can be informed about the current control parameter. Furthermore, it can be provided that the user can optionally interrupt an automated transmission of the control parameter, for example if he considers an updated control parameter to be unsuitable.

The at least one control parameter can be configured to establish an operating mode of the medical device. The at least one control parameter can comprise a parameter set. For example, the control parameter can cause a setting of a coagulation instrument for a specific tissue entity. In this case, the assessment comprises, for example, whether the object subregion is suitable for tissue coagulation and what type of tissue it is and/or what its surroundings are like. For example, through a comparison with a database, suitable parameters for the coagulation instrument can be ascertained for the accordingly detected scene. These can then be automated before the use of the instrument in the object subregion and/or transferred to the instrument after user approval in order to accordingly adjust it. It can also be provided that, as part of the assessment, a condition such as the humidity of tissue is ascertained, and it is assessed whether this is sufficient or whether additional humidification is required. Based on this, optimized setting parameters for a gas humidifier and/or an insufflator can be determined.

Alternatively or additionally, the at least one control parameter can be configured to cause a safety-relevant shutdown of the medical device. This can be useful, for example, when critical anatomical structures are present in a coagulation region, such as a ureter of a patient. The device interface and/or the output generation unit can be configured to automatically transmit the control parameter to the medical device, at least when it causes the safety-relevant shutdown. Alternatively, a warning can be output to the user, upon which the user approves the transmission of the control parameter, which causes the shutdown, to the medical device. In some embodiments, the assessment can comprise that the safety relevance of a performed and/or upcoming diagnostic and/or therapeutic activity is assessed. If it is assessed that the safety of the patient is at risk, for example due to an impending incision and/or an impending impact on a region that should not be accordingly impacted, the control parameter that causes the safety-relevant shutdown can be generated. In some embodiments, this is automatically output to the medical device even if the user can and/or must enable other, non-safety-related control parameters before they are output to the medical device.

A simple, reliable and user-friendly verification of the success of a performed diagnostic and/or therapeutic activity can be made possible in particular if the assessment comprises an evaluation of the quality of a diagnostic examination and/or a treatment result. The output can comprise information regarding the quality of the diagnostic examination and/or the treatment outcome. The evaluation can comprise at least a comparison with a database that contains information on different examination and treatment results. The assessment can comprise a binary and/or categorical, in particular nominally scaled or ordinally scaled quality parameter. Alternatively or additionally, the assessment can comprise a continuous quality parameter and/or be metric. The assessment of quality can concern the suitability of acquired image data for making a diagnosis. Furthermore, the assessment of quality can concern the success of a performed intervention. For example, it can be assessed whether tissue coagulation is sufficient to have the desired effect, such as complete and safe vessel sealing, whether a suture and/or one or more staples have been correctly applied, whether a structure has been successfully dissected, whether a ligation has been correctly performed, whether a biopsy has provided the required tissue samples, whether bipolar tubal sterilization has been successful, or the like. The information regarding the quality can be provided to the user during and/or immediately after the performed diagnostic and/or therapeutic activity. This allows the user to respond to the assessment of the quality if necessary and, for example, completely seal a partially sealed vessel, supplement an inadequate suture line, take additional tissue samples, select changed settings for imaging, etc.

The assessment can be based on at least two different sets of image data and comprise a comparison of the attribute of the object subregion at two different points in time. In some embodiments, the attribute is determined before and after performing a diagnostic and/or therapeutic activity. The comparison of the attribute before the diagnostic and/or therapeutic activity is performed, with the attribute afterward, allows any changes to be reliably detected. A first set of image data can serve as a reference with which a second set of image data is compared. The assessment can also comprise a comparison series in which gradual changes in the attribute are considered. In some embodiments, the comparison of different sets of image data can be used to evaluate the quality of a diagnostic examination and/or treatment outcome. The different sets of image data can be obtained in accordance with image tracking. In particular, a subsequently acquired set of image data is based on tracking according to an earlier acquired set of image data. Tracking can be based on spatial information and/or a white light image. The tracking can be carried out continuously, in particular also between the images that result in at least two different sets of image data. If tracking is used, it can be performed using, for example, an optical flow algorithm, a landmark-based algorithm or another suitable algorithm. Alternatively or additionally, a specific image region, such as a portion of a medical device and/or a characteristic body part, in particular determined within the scope of image segmentation, can be detected in the different sets of image data and, based on this detection, these can be related with regard to their spatial coordinates. In some embodiments, a localization of a considered object subregion can be carried out based on the particular spectral information.

According to one aspect, the analysis of the image data comprises image segmentation. This allows objects to be detected and/or tracked at least partially automatically, for example within the context of tracking. In particular, the analysis unit can be configured, using the image segmentation, to identify a medical device that is located at least partially in the object region. Image segmentation can be performed using the spatial information and/or using the spectral information of the image data. Image segmentation can be performed with respect to the spatial coordinates and/or according to a spectral criterion, for example according to values in one or more specific spectral ranges. For example, if spectral ranges are selected for which high or low absorption values indicate the presence of water, and/or fat, and/or protein, and/or hemoglobin, the image segmentation can be performed according to these spectral ranges. Spatial regions in which a certain content of water, and/or fat, and/or protein, and/or hemoglobin is present can then be automatically detected.

Alternatively or additionally, the analysis of the image data comprises tissue detection. This allows the considered scene to be evaluated very accurately automatically and the assessment to be carried out very precisely. Tissue detection can be performed in particular on the basis of image segmentation. For example, structures, such as organs, vessels, nerves, fascia and/or body parts, can be detected. Tissue detection can comprise a type, extent, wall thickness, nature and/or composition of the tissue. Furthermore, the tissue detection can also comprise a number, for example a number of blood vessels, nerves, fascia and the like. Tissue detection can be based on spatial and/or spectral information. The tissue detection can take place in several stages and can comprise, for example, a first detection, in particular a rough detection, on the basis of a segmentation of a white light image and/or an image for a single spectral band as well as a second detection, in particular a fine detection, on the basis of additionally evaluated spectral information.

In some embodiments, the analysis of the image data can comprise the detection of at least one medical device. This allows the imaged situation to be assessed with high accuracy. The detection of the at least one medical device can in particular comprise information about a type, and/or, an orientation, and/or a position, and/or a state of the medical device. An AI algorithm can be used to determine the type, and/or orientation, and/or position, and/or state of the medical device. For example, the position of the medical device can be detected using a segmentation model, such as U-Net, with a ResNet50 backbone. In so doing, 2D folds and/or 3D folds can be used. Alternatively or additionally, a detection model can be used, such as a YOLO algorithm, in particular when information about a type of medical device and/or a comprehensive bounding box is required, especially when only such information is required or when it is sufficient.

Models and/or algorithms for image segmentation and/or tissue detection and/or detection of a medical device can be trained with annotated data. A trained model created in this way can then be applied to new image data that was not used for training.

The analysis can comprise an assignment of the image data to three-dimensional data that relate to the object region. The image segmentation and/or tissue detection and/or detection of a medical device can be linked with a mapping, such as a 2D mapping and/or a 3D mapping, that is based on existing spatial data of the object region and/or on spatial data of the object region obtained by imaging without spectral information, such as white light imaging. In some embodiments, such mapping can involve the use of stereoscopic image data. Alternatively or additionally, mapping can be carried out with a partially or fully simulated spatial model, in particular with a 3D model. Spatial data can also come from a tracked system. For example, the image data can be compared with data that are provided by the medical device and/or a robot manipulating it, and which allow conclusions about a location, in particular a position and/or orientation, of the medical device. In principle, mapping can be done with spatial data that are/were obtained in real time, substantially in real time, and/or in advance. In some embodiments, verification can be performed with preoperative data. For example, image data, in particular spatial and/or spectral image data, can first be obtained at a specific position and/or in a specific viewing direction in order to calibrate and/or adjust the imaging device. This step is optional. Furthermore, spatially and spectrally resolved image data of the object region can be generated using the imaging device. Their analysis can optionally be based on the results of the mentioned adjustment and/or calibration step. Tissue structures and/or portions of a medical device detected in the context of an analysis of the image data can then be compared or verified with preoperative data that relate to the object region. This makes it possible to check, before tracking detected structures, whether the corresponding detection is correct on the basis of the spatially and spectrally resolved image data, for example whether an organ, a vessel, a body part, a nerve, a fascia, etc. was correctly detected. In addition, this allows tracking to be performed reliably even if the tracked structure is only partially represented in the spatially and spectrally resolved image data, since the assignment of this partial representation is based on the use of additional data.

In general, in some embodiments, it can be provided that the attribute comprises information about anatomical and/or physiological features of the object subregion. For example, the attribute can comprise a content of a particular substance, in particular a water content, a hemoglobin content, a fat content, a protein content or the like, a tissue coagulation state, in particular a vascular occlusion state, a geometry, coordinates, directional information, an amount and/or a direction of a blood flow, a blood flow state, a humidity and/or a dehydration state or the like.

Alternatively or additionally, the analysis can comprise information about anatomical and/or physiological characteristics of the object subregion. For example, the evaluation and in particular the evaluation parameter can comprise a content of a certain substance, in particular a water content, a hemoglobin content, a fat content, a protein content or the like, a degree of tissue coagulation, a geometry, coordinates, directional information, an amount and/or a direction of a blood flow, a blood flow state, a humidity and/or a degree of dehydration or the like. In this case, the attribute can be a classification and/or categorization based on the evaluation or the evaluation parameter. For example, the analysis can provide a metric and/or numerical evaluation parameter, such as an amount of a content, a volume, a length, an angle or the like, and the attribute can be based on a comparison of the evaluation parameter with one or more value ranges, each of which is assigned a category and/or designation, in particular nominal and/or ordinal. The assignment can be based on information from a database and/or from artificial intelligence and/or using an appropriately trained neural network. In this regard, reference is also made to the above description.

According to one aspect, the imaging device comprises a smoke detection unit and/or a contamination detection unit that is configured to detect a presence and/or absence of smoke and/or contamination in the object region and/or on an optical window. This makes it possible to automatically ascertain whether the conditions for successful or qualitatively satisfactory imaging are met. Smoke that was generated, for example, during energy input, such as in the context of tissue coagulation, and covers parts of the object region can be detected. The presence of contamination from tissue residues, blood, liquids, particles and the like on windows can be detected. The smoke detection unit and/or the contamination detection unit can be configured to perform the smoke detection and/or the contamination detection based on an AI algorithm using a white light image, for example a binary classification algorithm, such as ResNet 50. The object region can be imaged for this purpose. It can also be useful to adjust the focus to direct it more on potentially contaminated windows. Smoke detection and/or contamination detection can be performed based on the analysis. In particular, in some embodiments, the smoke detection and/or the contamination detection can be based on spectral information, for example on absorption values in characteristic spectral bands that allow conclusions about the presence of certain substances. It can be provided in this regard that smoke detection and/or contamination detection only takes place for a certain spatial selection of image data, for example for a region for which further image data is to be acquired.

Smoke and contamination can be efficiently automatically taken into account for generating an output or for an automatic assessment, in particular if the assessment unit is configured to take into account, in the assessment of the attribute, the presence and/or absence of smoke and/or contamination in the object region and/or on a window detected by the smoke detection unit and/or by the contamination detection unit. For example, the attribute can be assigned a quality value that depends on a degree of contamination and/or a degree of impairment of imaging by smoke. In this case, the output can be provided with the quality value or a parameter derived therefrom, in particular to indicate a possible impairment for a user. Alternatively or additionally, the image acquisition unit can be configured to regenerate image data of the object region at a time after the generation of the image data of the object region if the smoke detection unit and/or the contamination detection unit has detected the presence of smoke and/or contamination in the object region and/or on a window based on the image data of the object region. A waiting time applied here until this point in time can be fixed, specifiable by a user and/or adaptive.

A high degree of ease of use and/or intuitive comprehensibility of information addressed to a user can be achieved in particular if the output comprises at least one overlay addressed to a user which is superimposed on a pictorial representation of the object region. For example, the display unit can generate a pictorial representation of the object region that is based on spatial and/or spectral image data. This pictorial representation can be based on the spatially and spectrally resolved image data and/or on image data generated separately therefrom, for example on white light image data, and/or real-time image data, and/or image data that do not comprise spectral information or that are not multispectral or hyperspectral. The overlay can be superimposed on this display partially or completely. In some embodiments, the overlay can convey spectrally and spatially resolved information. For example, coloring can be done according to spectral data. The overlay can be generated with a different or the same refresh rate as the display. In particular, it can be provided that an image which is only substantially updated in real time and contains spectral information is superimposed on a real-time image which does not contain any spectral information. The overlay can alternatively or additionally contain information that was determined based on the spatially and spectrally resolved image data, but from which the image data itself is not apparent, for example categorical information, instructions, selected and/or selectable icons, predefined images, text, colors, warnings, etc.

Areas of interest to the user, such as certain body parts, structures, types of tissue, vessels, etc., can in particular be made identifiable very intuitively if the overlay comprises highlighting and/or coloring of at least regions of a pictorial representation of the object region. For example, the coloring can be done in at least two colors that express categories, such as "suitable" and "unsuitable", and/or "safe" and "dangerous", and/or "adequate quality" and "poor quality". The coloring can be based on a color scale. The color scale can be multi-level, in particular at least three-level, at least five-level or at least ten-level, or also continuous.

Alternatively or additionally, a visual output can be provided via colored lamps and/or via a separate display, in some embodiments via a display of the medical device. In this respect, the output unit can be at least partially formed by the medical device. The device interface, for example, can serve as an interface between the output generation unit and the output unit.

An easily perceptible output that can be registered by the user even if he temporarily takes his eyes off a display can be achieved in particular when output comprises at least an audio output directed to a user. The audio output can be output via the audio output unit. The audio output can comprise a tone, a sequence of tones, a noise, a voice output, music, or any combination thereof. The audio output can, in some embodiments, comprise a warning, for example, when a diagnostic and/or therapeutic activity is about to be performed incorrectly, and/or is being performed incorrectly, and/or has been performed incorrectly. In particular, a warning can be output if the user is about to work with the medical device in an unsuitable region, which could potentially pose health risks to a patient.

The output can concern a classification of tissue, in particular a classification according to the nature and/or type and/or condition of the tissue. This allows the user to quickly and easily see which tissue types and/or tissue structures are located in the object region.

A user can be guided in an intuitive manner during a diagnosis and/or treatment, in particular if the output comprises a suitability and/or unsuitability of at least one object subregion of the object region for the diagnostic and/or therapeutic activity to be carried out. The output can comprise an overlay for this purpose as it has been described above. In this way, the user can thereby be shown, for example by means of colored markings, arrows, visual highlights or the like, which regions of the object region are suitable, and/or unsuitable, and/or susceptible to injury, and/or not or not fully identifiable/classifiable. Based on this, the user can carry out the diagnostic and/or therapeutic activity in a targeted manner at a suitable location or generally in a suitable and safe way.

In some embodiments, the output can relate to the quality of a result of the performed diagnostic and/or therapeutic activity. To this end, the output can be binary and classify the quality as "OK" or "not OK", for example. It can also be provided that several quality levels are used, for example a point scale, a grading scale or a continuous scale. If, for example, the therapeutic activity was tissue coagulation in the object subregion, after implementation, it can be output whether or not the tissue coagulation in the object subregion was complete and/or sufficient. For example, if the therapeutic activity was tissue humidification using an insufflator that allows gas humidification of tissue, it can be output after humidification has taken place whether or not the humidification was sufficient. The result whose quality is assessed can also be an intermediate result and/or a continuously updated result or a state changing over time, such as in the mentioned example of tissue humidification.

Treatment errors and/or injuries to the patient can be avoided in particular if the output comprises a warning addressed to a user. The warning can be a visually output warning, and/or an audio warning, and/or a haptic warning. For example, if it is judged that the user is about to inadvertently damage and/or sever a vessel and/or nerve and/or fascia, the warning can be output in order to make the user aware of this. This can be in particular helpful in microinvasive interventions since the site cannot then be viewed directly by the user, but only an image thereof can be observed.

The analysis can comprise a comparison of normalized and/or standardized spectral data. This allows generated image data to be evaluated very efficiently. In addition, effects that are due to different-sized viewed regions can be eliminated if necessary. The normalized and/or standardized data can be normalized and/or standardized spectra. Normalization and/or standardization can comprise division by a value of the spectrum at a particular wavelength, normalization to an area under the curve, a subtraction of a background, etc. In the context of test experiments, typical spectra can be ascertained that characterize certain tissue types that have been therapeutically influenced in a certain way. For example, the absorption spectrum of coagulated tissue depends on the degree of coagulation and on the parameters used for coagulation. If image data are generated before and after a targeted energy input into the tissue and the spectral data are compared, deviations due to different observed amounts of tissue can be compensated for by normalizing and/or standardizing the spectra to be compared.

In some embodiments, the analysis can comprise a comparison of spectral data for different spectral ranges. This can increase the accuracy of an assessment by comprehensively taking into account characteristic spectral properties. For example, values of different spectra at several wavelengths and/or in several wavelength ranges can be compared. Furthermore, it can be provided that curve shapes are compared with each other. Curves based on models can be adapted partially or completely to spectra obtained from the image data. Models adapted in this way and/or their underlying parameters can then be compared with each other. For example, different amino acids have different absorption spectra, wherein many show a pronounced absorption in the 280 nm region. If only this one wavelength were considered, it might be difficult in certain circumstances to differentiate between amino acids or certain proteins in which certain amino acids occur with varying frequency. However, if data for several wavelengths are taken into account, characteristic absorption shoulders, for example, can be included in the assessment.

Expressed generally, spectral information can in many cases relate to the absorption of light. The spectral information can represent an absorption spectrum. Alternatively or additionally, the spectral information can also relate to an emission of light, for example fluorescence. In general, almost any spectral measurements can be used. The lighting device can function as a measuring light source for an absorption measurement and/or as an excitation light source for an emission measurement. In some embodiments, the imaging device can be operable in different measurement modes in which, for example, the image acquisition unit and/or the illumination unit are controlled differently in order to implement different measurement principles.

Various energy-injecting diagnostic and/or therapeutic activities have already been mentioned several times. Expressed generally, the diagnostic and/or therapeutic activity that is to be performed and/or has been performed can comprise an energy input into tissue, in particular a thermal and/or electrosurgical and/or radiation-based energy input. The medical device can accordingly be an energy-injecting instrument, for example a coagulation instrument, an HF instrument, a laser instrument, an electrosurgical device, an electroscalpel, an electrocauterizer and/or a vessel sealing device, etc.

The evaluation parameter can contain information regarding tissue coagulation, in particular regarding vessel sealing, tube sterilization and/or the welding and/or connection of tissue structures, such as the formation of anastomoses. If the output relates to a control parameter, this can in particular in this case be a process parameter, such as a power, a voltage, a current, a resistance, a phase shift, a tissue shrinkage, a temperature, a gripping force or the like.

A very versatile image acquisition unit can in particular be provided and/or a high degree of flexibility and quality of imaging can be achieved in particular if the image acquisition unit is configured to be multimodal and can be operated in at least a first mode in which spatially and spectrally resolved image data can be generated, and in at least a second mode in which only spatially resolved image data can be generated. The first mode can involve the above-described generation of image data. The second mode can involve white light image acquisition and/or image acquisition without spectral information. The image acquisition unit can have separate optical systems and/or image acquisition sensor systems, which can be switched between depending on the selected mode and/or which can be used simultaneously, or a common optical system and/or a common image acquisition sensor system.

An accurate, automatically generatable assessment and/or recommendation can be obtained in particular if the assessment is additionally based on patient-specific data that are different from the image data. The patient-specific data can be obtained from a database. The patient-specific data can reflect relationships between patient data, such as age, gender, weight, medical history, etc., and expected spatially and spectrally detectable properties, for example an expected water content in a certain organ of a patient with a certain prior history, an expected vessel diameter for a certain vessel of a patient of a certain gender and age, etc., wherein these examples only serve for illustration.

In some embodiments, the image acquisition unit can be stereoscopic. The stereoscopic design of the image acquisition unit can involve multispectral or hyperspectral image acquisition and/or image acquisition that only provides spatially resolved image data. In the case of stereoscopic image acquisition, the spatial data can be three-dimensional. Specifically, they can be data that describe a surface in three-dimensional space. The image data can then be four-dimensional and comprise, for example, three spatial coordinates and one spectral coordinate.

The invention further relates to a control unit comprising a processor and a memory, wherein program code is saved on the memory which, when it is executed by the processor, causes a method according to the invention to be carried out.

The invention further relates to program code which, when it is executed by a processor and/or a control unit and/or a computer, is configured to cause a method according to the invention to be performed.

Furthermore, the invention relates to a computer program product comprising a computer-readable medium and program code according to the invention saved on the computer-readable medium.

The device according to the invention and the method according to the invention should not be limited to the application and embodiment described above. In particular, the device according to the invention and/or the method according to the invention can have a number of individual elements, components and units as well as method steps, which differs from a number mentioned herein, in order to fulfill a function described herein. In addition, for the ranges of values specified in this disclosure, values within the stated limits shall also be deemed to be disclosed and to be usable in any manner.

It is in particular pointed out that all features and properties described with regard to the device, but also procedures, can be analogously transferred to the method according to the invention and can be used within the meaning of the invention and are considered to be co-disclosed. The same applies in the opposite direction. This means that structural features mentioned in relation to the method, i.e. features relating to the device, can also be taken into account, claimed and also counted as part of the disclosure within the scope of the device claims.

The present invention is described below by way of example with reference to the accompanying figures. The drawings, the description, and the claims contain numerous features in combination. A person skilled in the art will also, expediently, consider the features individually and use them in combination as appropriate in the context of the claims.

If there is more than one example of a particular object, only one of them may be provided with a reference sign in the figures and in the description. The description of this example can be transferred accordingly to the other examples of the object. If objects are named using numerical words, such as first, second, third object, etc., these are used to name and/or assign objects. Accordingly, for example, a first object and a third object may be included, but not a second object. However, a number and/or sequence of objects could also be derived using numerical words.

DETAILED DESCRIPTION

Figure 1:
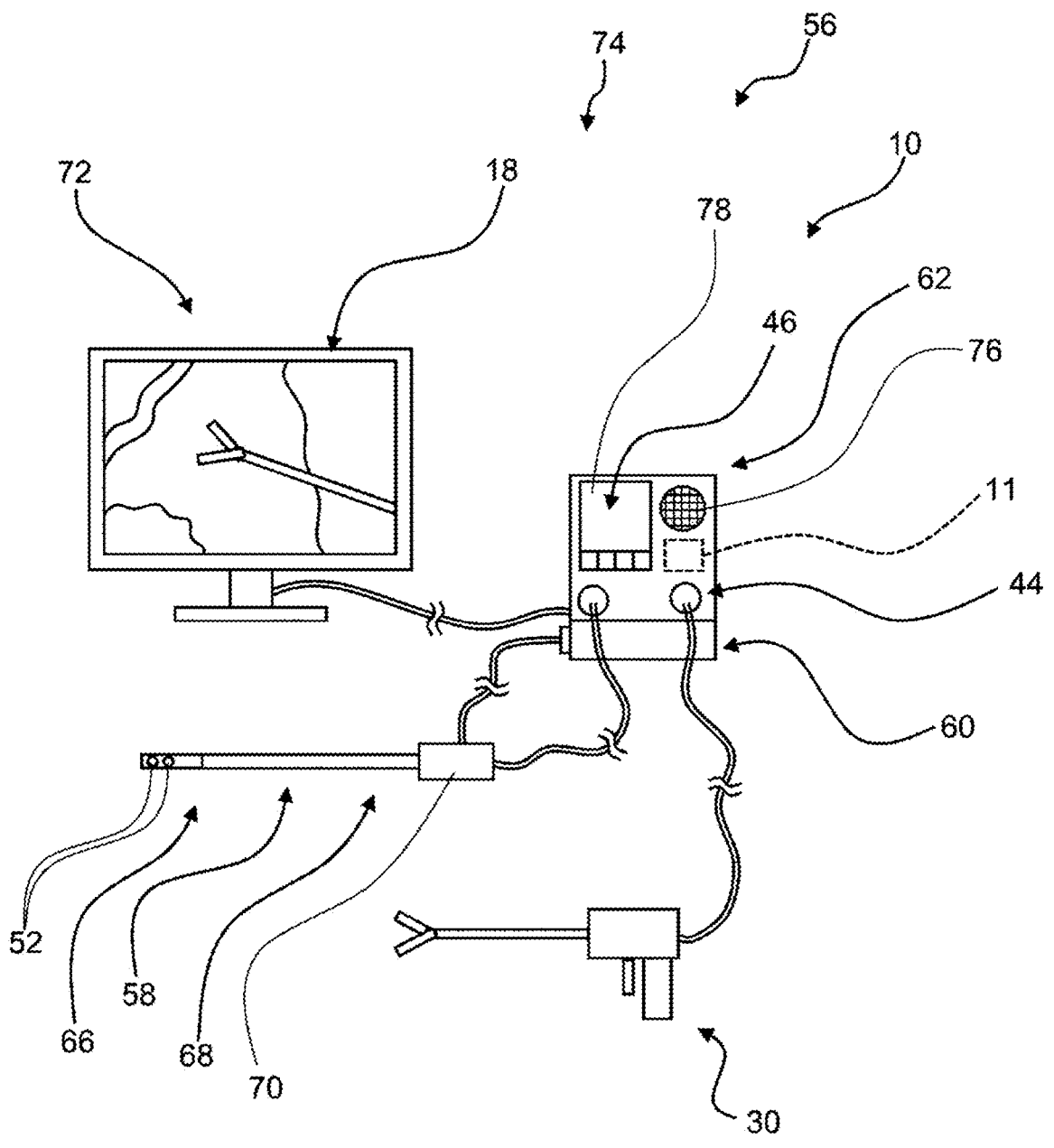
FIG. 1 is a schematic representation of a medical system with a medical imaging device.
Figure 2:
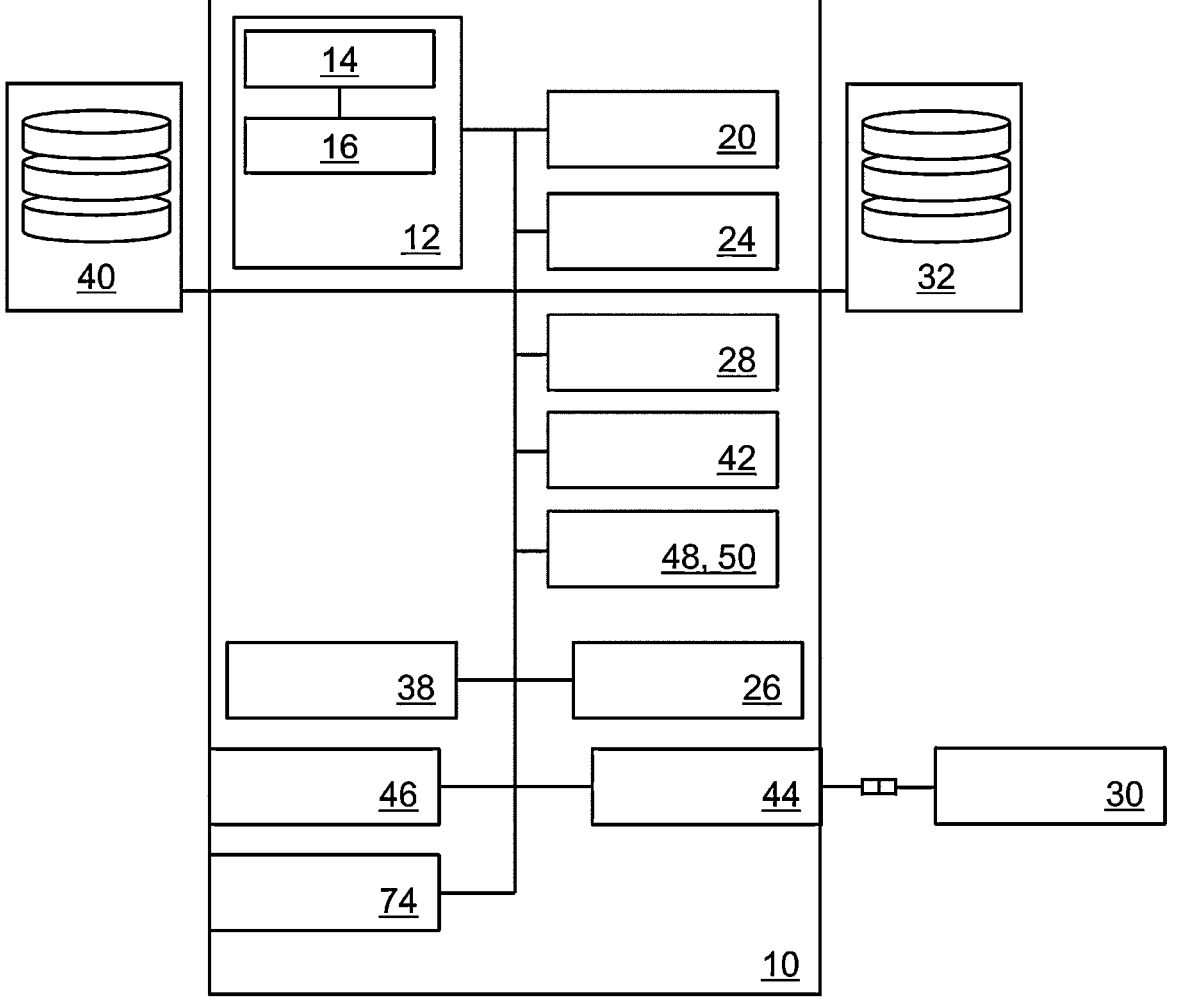
FIG. 2 is a schematic structural diagram of the medical imaging device.

FIG. 1 shows a schematic representation of a medical system 56 with a medical imaging device 10 and a medical device 30. A schematic structural diagram of the imaging device 10 and the medical device 30 is shown in FIG. 2. Both figures are referred to in part below.

In the instance shown by way of example, the imaging device 10 is an endoscopic imaging device, specifically an endoscope device. Alternatively, the imaging device 10 could be an exoscopic, a microscopic or a macroscopic imaging device. The medical imaging device is provided for an examination of a cavity.

The medical device 30 in the illustrated case is a bipolar electrosurgical instrument. The medical device 30 is configured to introduce energy into tissue in a targeted manner in order to coagulate it, for example for vascular occlusion. This design is to be understood purely as an example. Other types of energy injection can be provided, as well as other types of medical devices in general, such as surgical, diagnostic, imaging, intervention-supporting, anesthetic or other medical instruments and/or devices.

The imaging device 10 comprises, for example, a medical imaging unit 58. In the shown case, this is an endoscope. Furthermore, the medical imaging device 10 can comprise a lighting device 60. In the shown case, the lighting device 60 is connected to the imaging unit 58 via a light guide. Illumination light can therefore be guided to the imaging unit 58 and directed from there onto an object to be imaged, in particular a site.

The imaging device 10 has, by way of example, a control unit 62. The control unit is for example connected to the imaging unit 58 via a cable and/or an optical line and/or a light guide.

The imaging device 10 and in particular the imaging unit 58 has, by way of example, one or more windows 52 through which illumination light can be coupled out and/or object light can be coupled in.

The imaging unit 58 has a distal portion 66. The distal portion 66 is configured to be inserted into a cavity in an operating state. In the operating state, the distal portion 66 faces a patient in the operating state. In the operating state, the distal portion 66 is facing away from a user in the operating state. Furthermore, the medical imaging unit 58 has a proximal portion 68. In the operating state, the proximal portion 68 is arranged outside a cavity in the operating state. In the operating state, the proximal portion 68 faces away from the patient. In the operating state, the proximal portion 68 faces the user.

The imaging unit 58 has a handle 70. The handle 70 is by way of example configured for handling by the user. Alternatively or additionally, the handle can be configured for attachment and/or connection to a medical robot. The imaging unit 58 can also be integrally formed with a robot in some embodiments. A position and/or orientation of the imaging unit 58 relative to the patient is variable, for example by manipulation by the user and/or by appropriate movement of the robot.

The medical system 56 has a display device 72. The display device 72 can be part of the imaging device 10. The display device 72 can be a separate display such as a screen or the like. In other embodiments, the display device 72 can also be integrated into the imaging unit 58 and/or the control unit 62.

The imaging device 10 has a device interface 44 via which the medical device 30 can be connected to the imaging device 10. In the shown case, the device interface 44 is part of the control unit 62. In the shown case, the device interface 44 is wired. The device interface 44 is detachable. Furthermore, the device interface 44 is configured to connect to various medical devices. The device interface 44 can comprise a socket and/or electrical connectors. In some embodiments, the device interface 44 can also be partially or completely wireless, i.e. the medical device 30 can then be connected wirelessly, for example via a radio connection, to the imaging device 10, and the devices 10, 30 can have correspondingly suitable antennas.

The imaging device 10 has a user interface 46 through which the user can make entries. The user interface 46 can comprise a plurality of controls that can be attached to different components of the imaging device 10 and/or of the medical system 56.

The imaging device 10 has a spatially and spectrally resolving image acquisition unit 12 which has at least one optical system 14. The image acquisition unit 12 further comprises an image acquisition sensor system 16 coupled to the optical system 14. The optical system 14 and the image acquisition sensor system 16 are configured to generate image data of an object region 18. The object region 18 is shown in FIG. 1 by way of example on a display of the display device 72. The image data comprise both optical and spectral information. In the present case, the image data correspond to two-dimensional spatial data that define spatial pixels, as well as spectral data that are assigned to the individual pixels. A spectrum is therefore available for each pixel from the image data. In addition, a two-dimensional image is obtainable from the image data for each spectral band. The image data correspond to a multispectral or hyperspectral data cube.

The optical system 14 comprises optical elements (not shown) that collect object light and lead it to the image acquisition sensor system 16. The image acquisition sensor system 16 comprises a CMOS or CCD sensor (not shown). The optical system 14 and the image acquisition sensor system 16 are arranged together in a pushbroom arrangement. In other embodiments, a whiskbroom arrangement, a staring arrangement and/or a snapshot arrangement is used. In the present case, the image acquisition unit 12 is configured for hyperspectral image acquisition; the imaging device 10 is accordingly a hyperspectral imaging device. Regarding different methods of hyperspectral imaging and components required for this, reference is made to the article "Review of spectral imaging technology in biomedical engineering: achievements and challenges" by Quingli Li et al., published in Journal of Biomedical Optics 18(10), 100901, October 2013, and to the article "Medical hyperspectral imaging: a review" by Guolan Lu and Baowei Fei, published in Journal of Biomedical Optics 19(1), 010901, January 2014. In other embodiments, the imaging device 10 can also be multispectral. Several spectral ranges can be observed, for example, by filters that can be optionally inserted into an object light beam path and/or by sequential illumination with different wavelengths.

The image acquisition unit 12 is at least partially included in the imaging unit 58. Parts of the optical system 14 and/or the image acquisition sensor system 16 can be included in the control unit 62. For example, object light can be guided to the image acquisition sensor system 16 via a light guide, and this can be arranged in the control unit 62. In other embodiments, the entire image acquisition sensor system 16 is included in the imaging unit 58, and only data are transmitted to the control unit 62.

The imaging device 10 further comprises an image analysis unit 20. This is configured to create an analysis of the image data. The analysis is based on both spatial as well as spectral information. The analysis comprises at least one evaluation which comprises at least one evaluation parameter that relates to an object subregion 22 of the object region 18. This will be discussed in more detail below.

The imaging device 10 also comprises an assessment unit 24. This is configured to generate, based on the analysis and on the basis of information relating to a diagnostic and/or therapeutic activity that is to be carried out and/or has been carried out, an assessment of an attribute of the object subregion 22 that is relevant for the diagnostic and/or therapeutic activity. This will be discussed in more detail below.

The imaging device 10 further comprises an output generation unit 26 that is configured to generate an output based on the assessment.

In the exemplary case, the imaging device 10 comprises an output unit 74. The output unit 74 can comprise the display device 72 and/or other output devices. In the shown case, the output unit 74 comprises, in addition to the display device 72, a loudspeaker 76 and an additional display 78 which are formed, for example, on the control unit 62. In other embodiments, the output unit 74 has an interface for connecting one or more output devices. The output generation unit 26 can also comprise the output unit 74 or its components.

The imaging device 10 comprises a control unit 11. This comprises a processor, a random access memory, a memory and appropriately configured circuits. Program code is stored on the memory and, when it is executed by the processor, causes the methods described herein to be carried out, or implements functionalities of the described units.

In the present exemplary embodiment, the imaging device 10 is multimodal. It can be operated both in a white light mode as well as in a multispectral mode or hyperspectral mode. In white light mode, only a white light image, which does not contain any spectral information, is acquired by the image acquisition unit 12. In multispectral mode or hyperspectral mode, however, the described spatially and spectrally resolved image data are generated. In the present case, the image acquisition unit 12 is configured to use both modes simultaneously by means of several optical systems and image acquisition sensors. In many cases, image acquisition with spectral information takes more time than pure white light imaging or imaging without spectral information. In the present case, it is therefore provided that images from both modes can be combined. Spatial information that is based on white light images is therefore subject to a higher refresh rate or acquisition rate than spatially and spectrally resolved image data. The former can be generated and/or output in real time, the latter substantially in real time.

However, it is understood that the functions, methods and method steps described below can also be based solely on the spatially and spectrally resolved image data that were obtained by means of multispectral and/or hyperspectral image acquisition.

Depending on the application, it can be advantageous to combine hyperspectral imaging with white light imaging parallel and/or alternating therewith, or to use multispectral imaging and, optionally, to use it without white light imaging. In many cases, multispectral imaging allows a higher refresh rate, so that real-time white light imaging can be dispensed with in certain circumstances. Hyperspectral imaging is characterized in many cases by a lower refresh rate but can provide higher spectral resolution. In this case, a combination with white light imaging is recommended in order to still have real-time image data available. Multispectral image data can also alternatively or additionally be used to monitor certain parameters or image regions in the background, optionally without displaying a corresponding image to the user. In particular in this case, a combination with white light imaging can also be advantageous for multispectral imaging.

Figure 3:
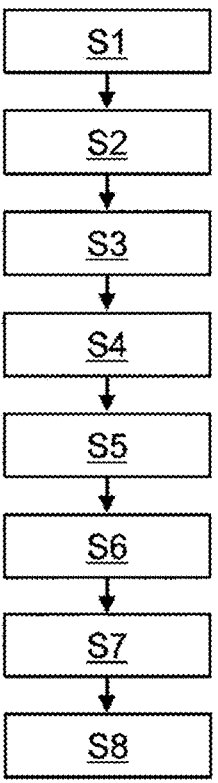
FIG. 3 is a schematic flow chart of a method for operating the imaging device or a method for medical imaging.

In the following, an exemplary application of the medical system 56 is described using the example of vessel sealing to be performed. However, it is understood that for other diagnostic and/or therapeutic activities, appropriate adaptations can be made, and/or one or more other medical devices 30 can be used. Reference is again made to FIG. 3 which shows a schematic flow chart of a method for operating the imaging device 10 or the medical system 56. FIG. 3 also analogously illustrates a method for medical imaging, carried out by means of the imaging device 10 or by means of the medical system 56.

Figure 4:
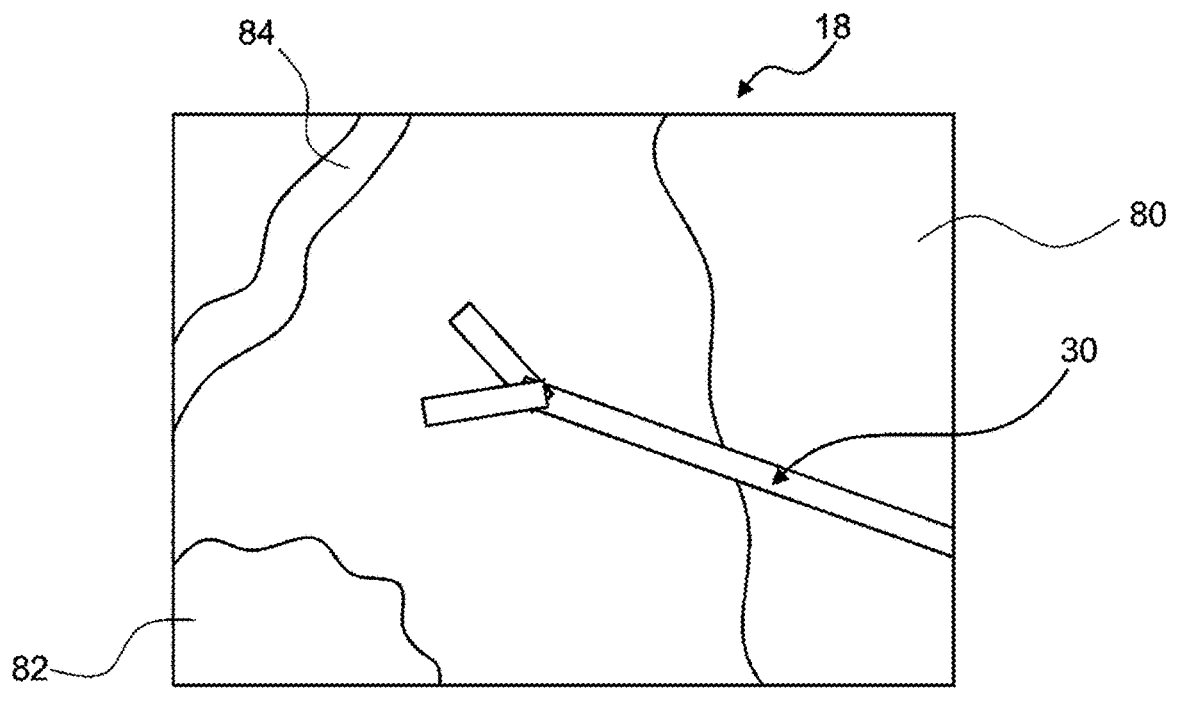
FIG. 4 is a schematic representation of an imaged object region.

FIG. 4 shows a schematic representation of an imaged object region 18. The object region 18 is observed in the context of a microinvasive procedure. For this purpose, the distal portion 66 of the imaging unit 58 is inserted into a cavity. The cavity contains various native structures 80, 82 as well as a vessel 84, for example a blood vessel, which is to be sealed. The sealing should be carried out by means of the medical device 30 by tissue coagulation at a suitable location.

In a step S1, spatially and spectrally resolved image data of the object region 18 are generated. For this purpose, the object region 18 is illuminated, and object light coming from the object region 18 is then detected. In the present case, the detected spectral information concerns light absorption. For each pixel, an absorption spectrum can correspondingly be obtained.

In a step S2, the image data are analyzed by the image analysis unit 20. The analysis comprises image segmentation and a comparison of spectral information with information that is saved in a database 32 and concerns properties of various structures, tissue entities, etc. Regions detected in the context of image segmentation can be analyzed for their spectral properties. The database 32 stores, for example, which tissue entities are typically characterized by which absorption spectra and/or show certain absorption values for certain spectral bands, in particular relative to other spectral bands. In the context of the analysis, an evaluation is created that comprises at least one evaluation parameter. The evaluation parameter can, for example, indicate which tissue entity is in the corresponding image segment. In the context of the analysis, the medical device 30 is also detected.

Figure 5:
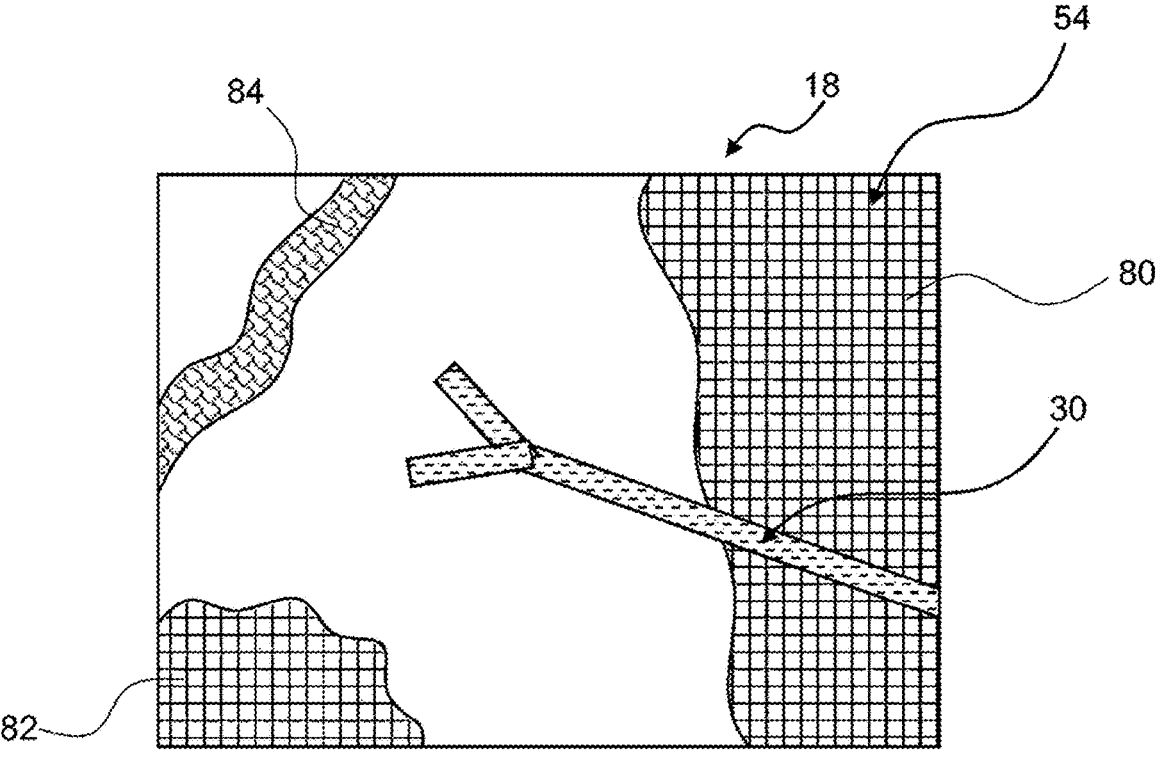
FIG. 5 is a schematic representation of the object region with an overlay of detected tissue structures.

In an optional step S3, an overlay 54, which can be displayed to the user, is generated on the basis of the evaluation. As illustrated in FIG. 5, the different detected tissue entities are highlighted differently, for example by overlaying a colored overlay, a texture, a label, or a combination. The user can therefore easily understand which subregions, instruments, organs, vessels, nerves, fascia, etc. are located in the object region 18.

Steps S2 and S3 can be repeated. As mentioned, a real-time white light image can be used as a basis. The overlaid highlights of different tissue structures based on spectral information can be updated substantially in real time.

In the present case, the detection of image regions involves tracking using a suitable tracking algorithm. In so doing, the corresponding highlighting can also be tracked even though no updated spectral image has yet been acquired and/or analyzed. For example, if the vessel 84 is detected and highlighted as such, but then moves in the object region and/or relative to the imaging unit 58, the highlighting can also be tracked using tracking based on a real-time white light image. If a new spectral image is available, its analysis can be used to check whether the current highlighting is still correct or needs to be adjusted.

In some embodiments, the detection is also based on 3D data that, for example, has been obtained from the database 32 and/or obtained using an additional detection step. If, for example, the imaging unit 58 is attached to a robot, the latter can first traverse the object region in a targeted manner in order to record a plurality of 2D images from which a 3D model can be created. The 3D data can be compared with the current image data, whereby structures can be detected even if they are only partially detectable and/or if they are temporarily obscured due to a changed viewing angle or due to movements in the object region 18.

In a step S4, an assessment is generated by the assessment unit 24. This is based on the evaluation parameter and on additional information, also termed herein as assessment information. The assessment information can be obtained from the database 32 and/or saved in the imaging device 10. In the present case, the assessment information contains information on which tissue entities are suitable and unsuitable for the planned therapeutic activity. The assessment information can be based on the empirical values of different doctors, clinicians, scientists, etc. as well as on different studies, medical findings or the like.

The imaging device 10 comprises a recommendation unit 28. The recommendation unit 28 can be part of the assessment unit 24. The recommendation unit 28 creates a recommendation for the user. This can be done in a step S5. The recommendation unit 28 determines, on the basis of the assessment and using information from the database 32 and/or a recommendation database 40, that an object subregion 22 is very well suited for the planned therapeutic activity. The recommendation database 40 can be integrated into the database 32 or formed separately therefrom. The database 32 and/or the recommendation database 40 contains information about characteristics of tissue entities, patient data, medical devices, diagnostic methods, therapeutic methods, etc., with which the attributes determined during the assessment can be classified and/or sorted. For example, the attributes that are assigned to the different image regions can be sorted according to their suitability or unsuitability for the therapeutic activity to be performed. Based on this, the recommendation unit 28 can determine an object subregion 22. At this point, vessel sealing can probably be carried out successfully. The recommendation unit 28 therefore recommends the object subregion 22 as the target location for tissue coagulation. Furthermore, the recommendation unit 28 classifies the structures 80, 82 as risk structures 34, 36 because an accidental use of the medical device 30 in the region of these structures 80, 82 would be very dangerous.

Figure 6:
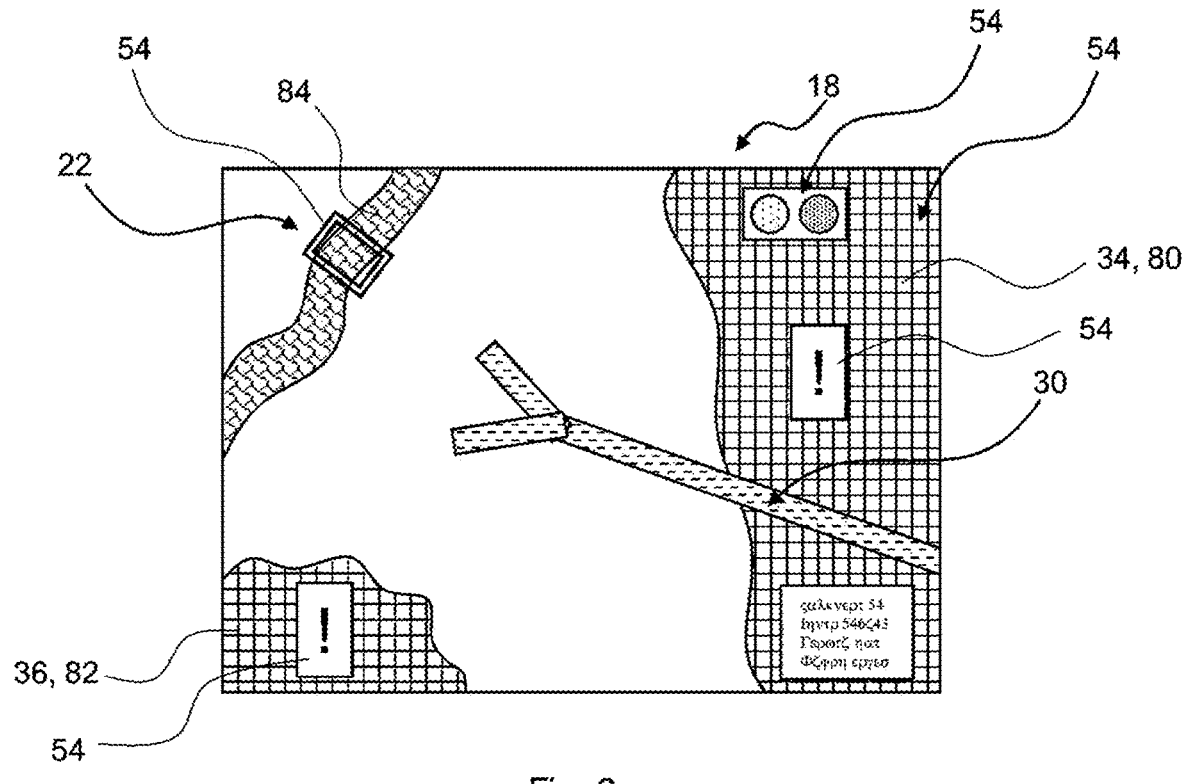
FIG. 6 is a schematic representation of the object region with different overlays of detected tissue structures.

On the basis of the assessment and the recommendation, the output generation unit 26 generates an output in the form of further overlays 54, as shown by way of example in FIG. 6. These include, for example, highlighting of the object subregion 22 in order to identify it as a preferred region for treatment, as well as colors, markings or the like in order to identify the risk structures 34, 36.

In other embodiments, the recommendation can also include that the user is advised to use or not to use a certain medical device. For example, a user can select which treatment outcome is to be achieved before a medical device is connected and/or inserted. Based on the recommendation, he can then choose the appropriate medical device from several possible ones. This selection can in particular also comprise an adaptation of a medical device by attaching a certain instrument tip or a certain attachment or the like.

In the present case, it is additionally provided that the output comprises a warning addressed to the user. For this purpose, for example, an overlay 54 in the form of a traffic light symbol is used, which switches to red if the user is about to act on a risk structure 34, 36. However, as long as the user moves the medical device 30 in non-critical regions and/or towards the object subregion 22, the traffic light symbol is displayed green. Additionally or alternatively, a warning tone or another audio signal can also be emitted by the output unit 74, in particular by the loudspeaker 76, if there is a risk of incorrect treatment.

The warning can also refer to procedures carried out during the performance of the diagnostic and/or therapeutic activity. For example, a warning can be issued if the user grasps tissue in a wrong place and/or with an inappropriate gripping force.

The imaging device 10 comprises an evaluation unit 38. This determines an evaluation of a generated recommendation based on an observed behavior of the user. For example, if the object region 22 is recommended for treatment and the user follows the recommendation, the recommendation is evaluated as good. However, if the user selects a different region for treatment, the recommendation will be evaluated as bad. The evaluation can be based on other parameters, such as experience of the user and/or treatment success. A data record associated with the recommendation can then be transmitted to the recommendation database 40 and used for future recommendations. A learning system is thereby provided.

The imaging device 10 further comprises a parameter determination unit 42. The parameter determination unit 42 is configured to determine at least one control parameter for controlling the medical device 30 on the basis of the assessment of the attribute of the object subregion. The output then contains this control parameter. The control parameter can be transmittable to the medical device 30 via the device interface 44.

The parameter determination unit 42 determines suitable parameters for the object subregion 22 for controlling the medical device 30. This can be done in a step S5. On the basis of the spectral and spatial image data that are available for the object subregion 22, as well as taking into account empirical values, manufacturer information, etc. which are saved in the database 32 and/or the recommendation database 40, the parameter determination unit 42 can determine process-relevant parameters that promise treatment success. The process and its effectiveness can therefore be optimally adapted to the tissue to be treated. The process-relevant parameters comprise, among others, the specification of the size and temporal progression (mode) of the energy introduced via the applied voltage and/or the type of regulation of the process, and/or via measured process parameters, such as power, voltage, current, resistance, phase shift, tissue shrinkage (thickness), temperature, gripping forces (tissue pressure), etc.

The output generation unit 26 is configured to generate an output of the parameters determined to be suitable for the user. These can be displayed, for example, as an overlay 54 in a box and/or as a list. The user can confirm the acceptance of the parameters by entering them, or can adjust them as required. The corresponding control parameters are then automatically transmitted to the medical device 30 via the device interface 44.

In an automatic mode, control parameters can be adjusted even without user acknowledgment. If the user activates the automatic mode, control parameters of the medical device 30 are automatically adjusted in ongoing operation.

In the present case, the parameter determination unit 42 also determines at least one control parameter that defines an activation state of the medical device 30. A two-stage security concept can therefore be implemented. In addition to warnings issued to the user, the medical device 30 can be automatically shutdown based on such a control parameter when, for example, gross misuse occurs, an image signal suddenly stops, the object region shifts by a large amount, severe bleeding is detected, or the like. An emergency shutdown can then occur even without the intervention of the user in order to prevent further consequences for the patient.

Both the suggestion of parameters to the user and automatically transmitted parameters can be adjusted substantially in real time when this is indicated based on the assessment of updated image data.

Figure 7:
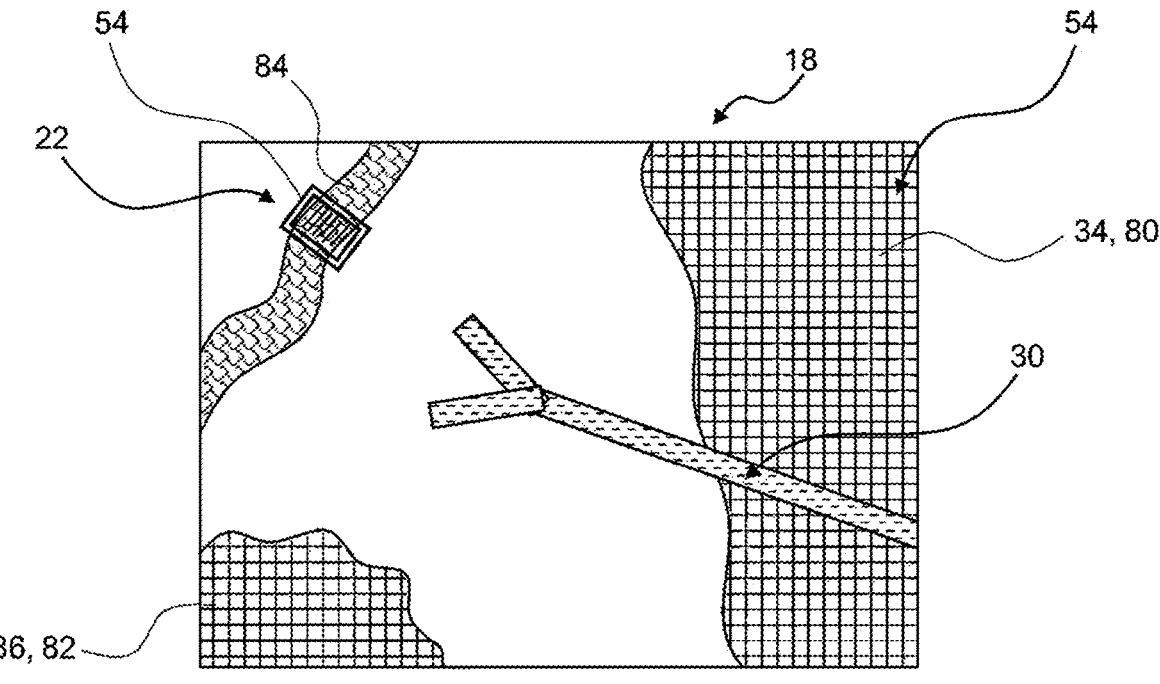
FIG. 7 is a schematic representation of the object region after carrying out a therapeutic activity with different overlays.

After the user has carried out the therapeutic activity in the object subregion 22, in particular after selecting and/or adjusting the suggested parameters, a new image can be recorded in a step S6. In particular, the actual performance of the diagnostic and/or therapeutic activity is not part of the methods described herein. As shown in FIG. 7, the tissue in the object subregion 22 has changed due to the performed therapeutic activity. This will be discussed further below.

Figure 8:
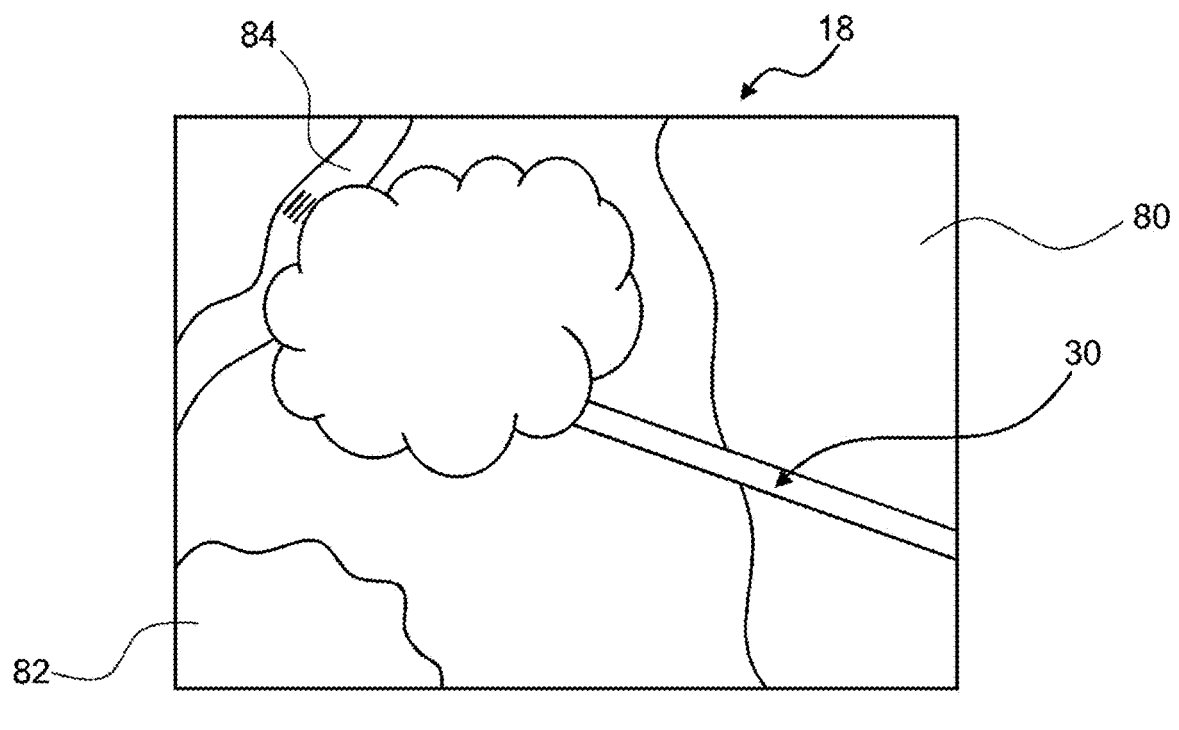
FIG. 8 is a schematic representation of the object region in the event of smoke formation in the object region.

In an optional step S7, the quality of the obtained image data can be assessed. In the present case, the imaging device 10 comprises a smoke detection unit 48 and a contamination detection unit 50. These are configured to detect smoke or contaminants. As shown in FIG. 8, due to the performed diagnostic and/or therapeutic activity, smoke symbolized by the illustrated cloud, can have arisen in the object region, for example due to vaporized and/or burned tissue. This smoke prevents the recording of high-quality images.

Figure 9:
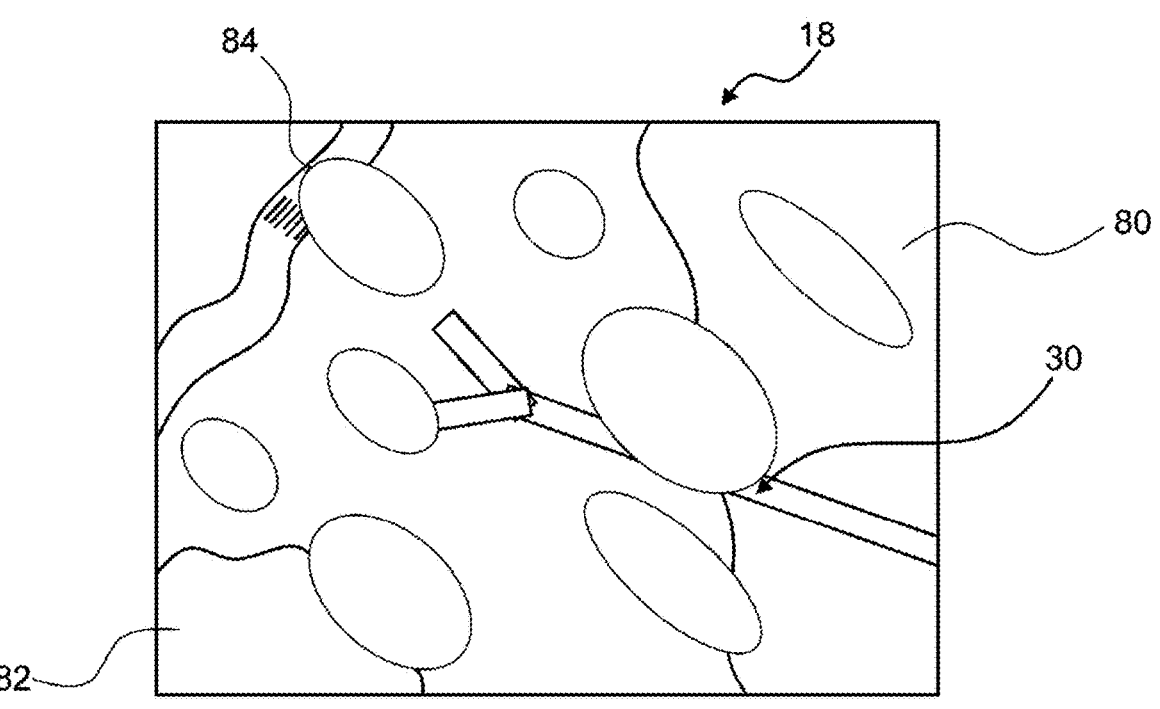
FIG. 9 is a schematic representation of the object region in case of the presence of contamination.

Furthermore, contaminants on one or all of the windows 52 can lead to reduced image quality. As schematically illustrated in FIG. 9, image artifacts can arise therefrom that can impair the quality of the image data.

The smoke detection unit 48 is configured to detect the presence of smoke based on the image data. For this, the smoke detection unit 48 uses an AI algorithm, such as a binary classification with ResNet 50. If smoke is detected, there can be a corresponding output to the user. In addition, the smoke detection unit 48 is configured to generate a waiting time. After expiration of the waiting time, it can be expected that the smoke will have cleared and image data of satisfactory quality can be generated again. In other embodiments, the smoke detection unit 48 can also examine all recorded image data and in each case release or identify them as possibly containing smoke or not release them.

The contamination detection unit 50 works in a similar way. If contaminants are detected that could significantly impair imaging, the user can be informed. In some embodiments, the imaging device 10 can also have a cleaning mechanism that can automatically clean the windows 52 as needed. In some embodiments, parameters for cleaning can be determined by the parameter determination unit 42 and passed on to the cleaning mechanism automatically and/or upon user approval. The cleaning mechanism can be a medical device within the meaning of this disclosure.

It is understood that the detection of smoke and/or contaminants can be performed at any time, for example at regular intervals and/or image acquisition intervals, upon user request, before each image acquisition, etc.

In a step S8, the image data of the treated object region are analyzed. In the present case, absorption values in different spectral ranges are used as evaluation parameters, which were obtained for image points located in the object subregion 22.

Figure 10:
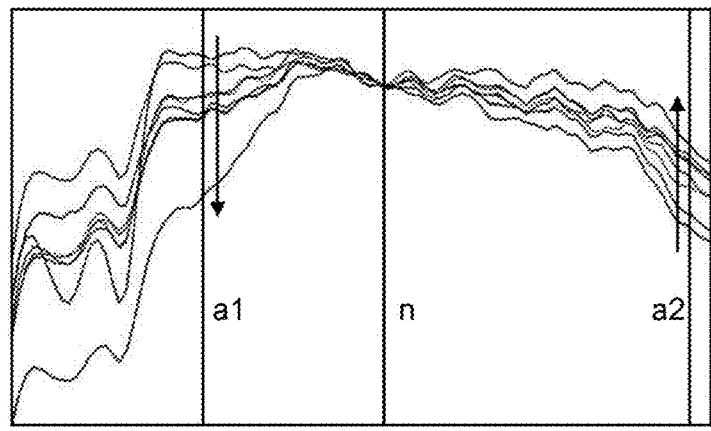
FIG. 10 is a schematic representation of absorption curves of tissue with different degrees of coagulation.

FIG. 10 shows schematic absorption curves in the visible and near-infrared range of tissue that was coagulated with different parameters. The inventors have found that the absorption curves for less and more strongly coagulated tissue behave differently in different spectral ranges. In a short-wave range, which is indicated by the line a1 in FIG. 10, the absorption decreases with increasing coagulation. In a long-wavelength range, which is indicated by line a2 in FIG. 10, the absorption increases with increasing coagulation. The spectra in FIG. 10 are normalized, in this case by division by the particular absorption value at line n. As described below, based thereon, an analysis and assessment can be made of whether a coagulation treatment has been completed with sufficient quality.

The analysis is based on a before-and-after comparison, wherein image data serves as a reference before the diagnostic and/or therapeutic activity is performed. The before-and-after comparison includes a difference calculation that indicates the extent to which the absorption has changed in the considered spectral ranges. To compensate for effects that are due to different amounts of tissue in the object subregion or other deviations, the spectra to be compared are normalized as illustrated in FIG. 10. In the present case, for example, the differences between lines a1 and a2 are determined as evaluation parameters.

Which ratios, differences and/or other relationships between these evaluation parameters can provide information about the quality of coagulation are saved in the database 32. The evaluation unit 24 used this information as evaluation information and, based thereon, assesses the evaluation parameters obtained from the analysis. In the present case, in this assessment, a binary attribute is determined that can assume the values "coagulation complete" and "coagulation incomplete". As mentioned above, the attribute can also for example refer to a grading scale and/or assume continuous values.

Figure 11:
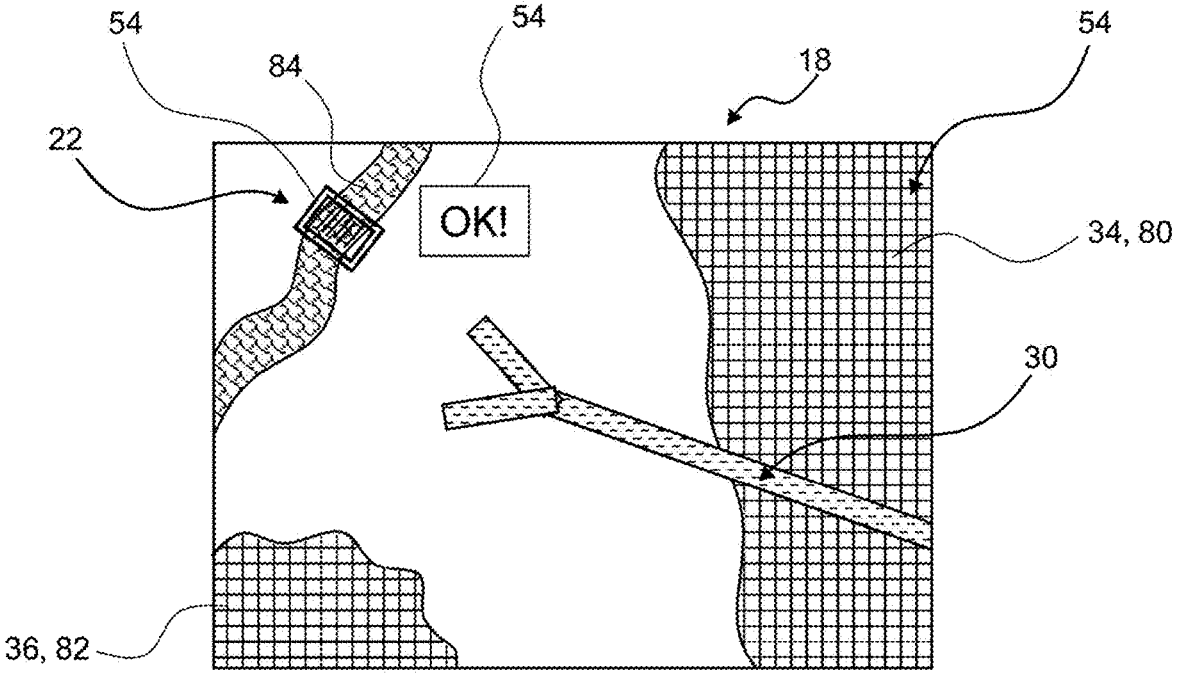
FIG. 11 is a schematic representation of the object region after carrying out a therapeutic activity with different overlays.

Based on the attribute, the output generation unit 26 generates an overlay 54 as output from which the user can extract the attribute and therefore the quality of the coagulation. This is illustrated in FIG. 11 by the display of the word "OK!". In other embodiments, the object region 22 can also be colored, for example green for good quality and red for poor quality.

In the described case, the spectra of all pixels in the object subregion 22 can be averaged to perform the analysis. In some embodiments, a similar attribute can also be determined point by point, for example, per pixel of the object region 22. The output can then comprise a corresponding point-by-point coloring, from which the user can determine at which points the coagulation was successful or inadequate.

It is understood that in addition to the automated detection of the object region, it can also be provided that the user can select and/or specify the object region. For example, in this way, he can highlight regions for which he would like to have a degree of coagulation assessed.

If necessary, further diagnostic and/or therapeutic activity can be planned and/or carried out, for example to achieve the desired degree of coagulation by follow-up treatment. An assessment can then be made again.

Aspects of the above description can also be summarized or described as follows. First, reference is made to FIG. 12. This shows a schematic flow chart of a method for operating the medical imaging device. A step S11 comprises an at least partially automated generation/acquisition of image data. A step S12 comprises an at least partially automated creation of an analysis of the image data, which is based on spatial and spectral information, wherein the analysis comprises at least one evaluation which comprises at least one evaluation parameter which relates to an object subregion 22 of an object region 18. A step S13 comprises an at least partially automated generation, based on the analysis and on the basis of information relating to a diagnostic and/or therapeutic activity that is to be carried out and/or has been carried out, of an assessment of an attribute of the object subregion 22 relevant to the diagnostic and/or therapeutic activity, which assessment is based on the evaluation parameter. A step S14 comprises at least partially automated output of an output that is based on the assessment.

Figures 12, 13:
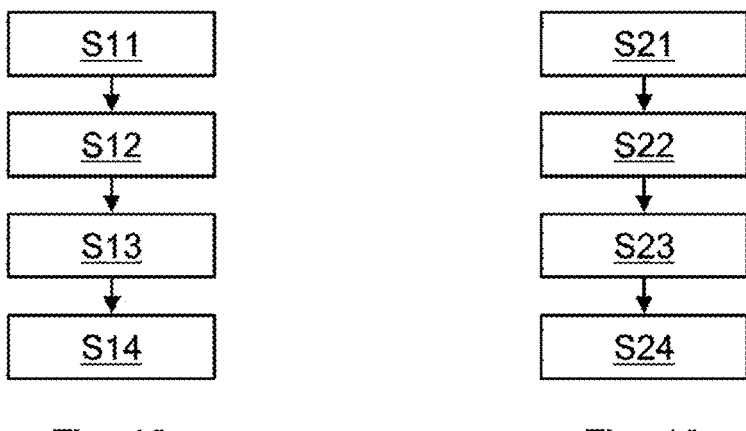
FIG. 12 is a schematic flow chart of a method for operating the medical imaging device.
FIG. 13 is a schematic flow chart of a method for medical imaging.

In the following, reference is made to FIG. 13. This shows a schematic flow chart of medical imaging. A step S21 comprises an at least partially automated generation/acquisition of image data. A step S22 comprises an at least partially automated creation of an analysis of the image data, which is based on spatial and spectral information, wherein the analysis comprises at least one evaluation which comprises at least one evaluation parameter which relates to an object subregion 22 of an object region 18. A step S23 comprises an at least partially automated generation, based on the analysis and on the basis of information relating to a diagnostic and/or therapeutic activity that is to be carried out and/or has been carried out, of an assessment of an attribute of the object subregion 22 relevant to the diagnostic and/or therapeutic activity, which assessment is based on the evaluation parameter. A step S24 comprises at least partially automated output of an output that is based on the assessment.

Figure 14:
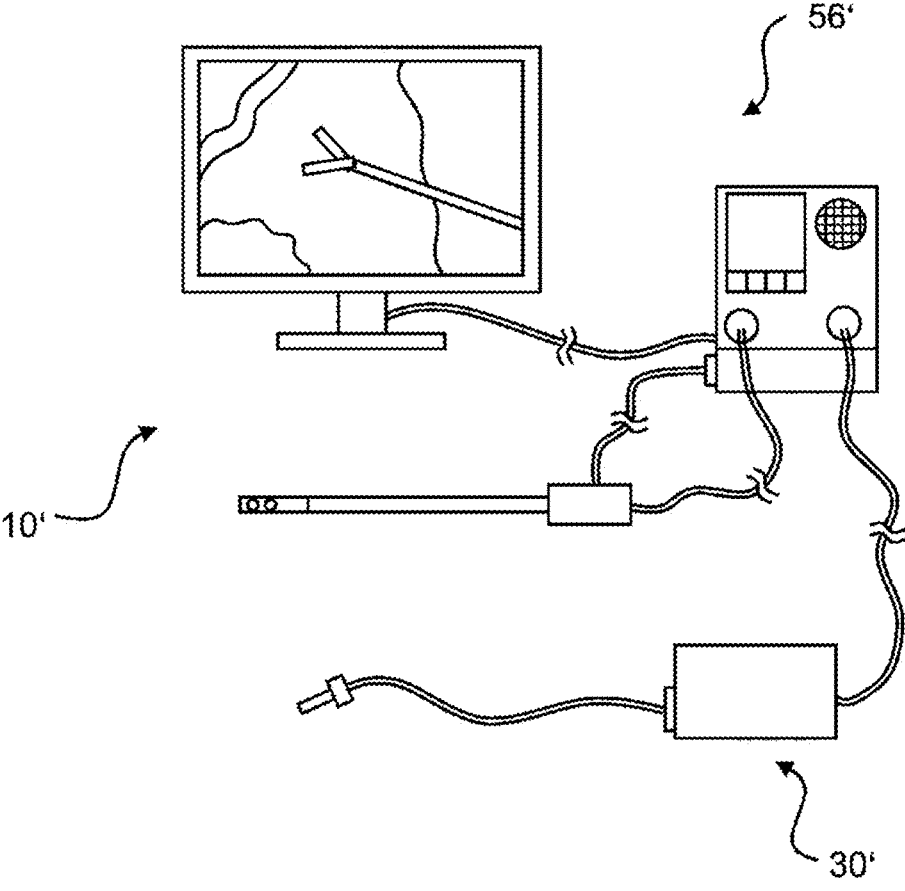
FIG. 14 is a first alternative medical system.

FIG. 14 shows a first alternative medical system 56'. The same reference signs denote objects that correspond to each other, wherein the reference signs in FIG. 14 are provided with apostrophes for differentiation. The medical system 56' comprises a medical imaging device 10' which is basically constructed like the above-described imaging device 10. The identification of the individual components with reference signs has therefore been omitted.

The medical system 56' comprises a medical device 30'. This is connected and/or connectable to the imaging device 10'. The medical device 30' is an insufflator. The medical device 30' is configured to perform gas humidification of tissue during an intervention. The imaging device 10' comprises a parameter determination unit that is configured to determine control parameters for the medical device 30'. These can be passed on to the medical device 30' as described above, in particular automatically. In the present case, the control parameters comprise a type and/or composition of the employed gas, typically carbon dioxide, a degree of humidification of the gas, a gas flow, a pressure, a humidification interval, etc. By means of the imaging device 10', it can be assessed whether a current setting of the medical device 30' is suitable for humidifying the tissue or whether the setting needs to be changed. For this purpose, evaluation parameters and attributes similar to those described above can be obtained from the gained spatially and spectrally resolved image data, from which parameters and attributes the degree of humidification of the tissue is evident. In the present case, the water content of the tissue is ascertained from the obtained spectra. This is compared with saved values in a database.

Figure 15:
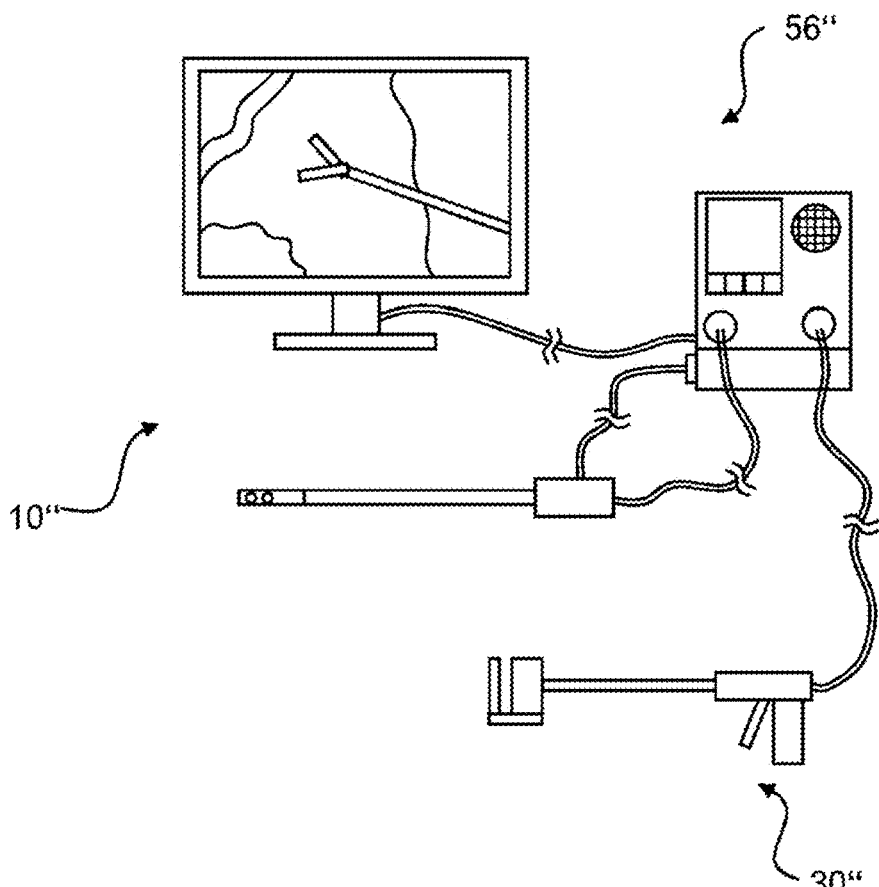
FIG. 15 is a second alternative medical system.

FIG. 15 shows a second alternative medical system 56". The same reference signs denote objects corresponding to each other, wherein the reference signs in FIG. 15 are each provided with two apostrophes for differentiation. The medical system 56" comprises a medical imaging device 10" which is basically constructed like the above-described imaging device 10. The identification of the individual components with reference signs has therefore been omitted.

The medical system 56" comprises a medical device 30". This is connected and/or connectable to the imaging device 10". The medical device 30" is a suturing device, in the shown instance a linear stapler. The medical device 30" is configured to create a suture, to connect tissue with staples, or the like during an intervention. The imaging device 10" comprises a parameter determination unit that is configured to determine control parameters for the medical device 30". These can be passed on to the medical device 30" as described above, in particular automatically. In the present case, the control parameters comprise, for example, a regulation of the closing forces of the clamps depending on an ascertained tissue condition. Furthermore, by means of the imaging device 10", it can be assessed whether staples have been applied in the correct place and/or in the correct number, or where additional staples are to be applied in order to form a seam with the desired quality. In so doing, patient-specific data, such as the gender or age of the patient, can be taken into account. This makes it possible to estimate the expected healing behavior of the created suture.

Figure 16:
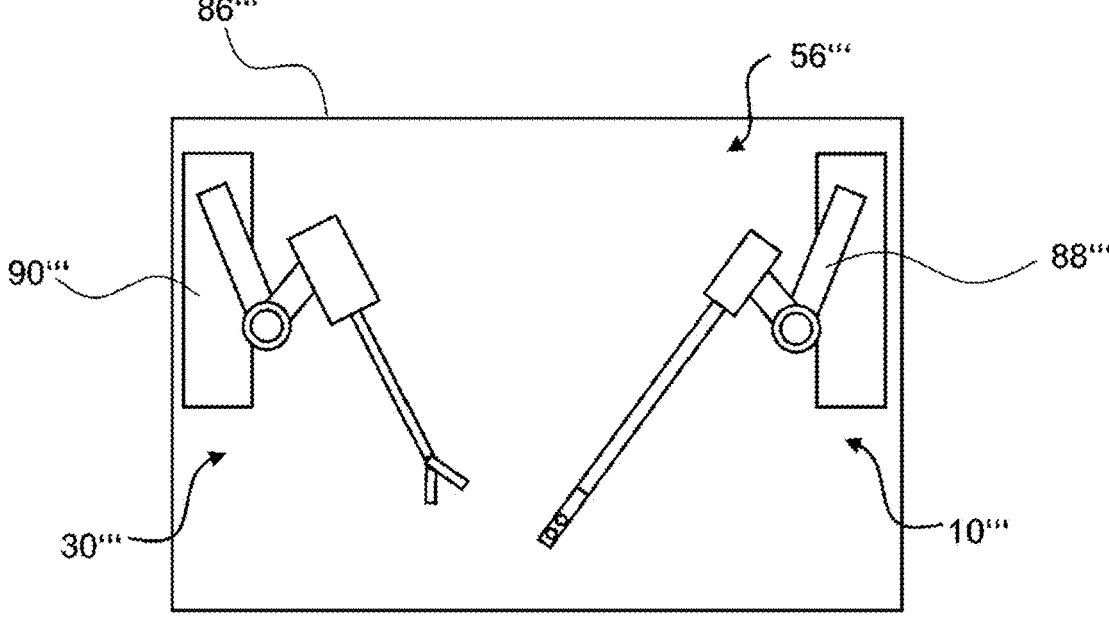
FIG. 16 is a third alternative medical system.

FIG. 16 shows a third alternative medical system 56'". The same reference signs denote objects corresponding to each other, wherein the reference signs in FIG. 16 are each provided with three apostrophes for differentiation. The medical system 56'" comprises a medical imaging device 10'" which is basically constructed like the above-described imaging device 10. The identification of the individual components with reference signs has therefore been omitted.

The medical system 56'" is part of a surgical robot 86'" or attached to such a one. For example, an imaging unit of the imaging device 10'" and a medical device 30'" are each attached to a manipulator 88", 90". These can therefore be moved and rotated, i.e. their position and/or orientation relative to the site can be automatically changed. In particular, when using such a robot 86'", the position and/or orientation of the imaging device 10'" or its imaging unit and/or the medical device can also be ascertained by means of the sensor system of the robot 86'". This can be in addition to image-based tracking or can replace it. The robot 86'" can also be part of the medical system 56'".

As already mentioned above, the methods described herein can also be performed partially or completely virtually, for example within the context of training and/or using a virtual surgery planner.

Aspects that contribute to the understanding of the invention are described below:

Aspect 1. Medical imaging device (10), in particular endoscopic imaging device, comprising:

a spatially and spectrally resolving image acquisition unit (12) which comprises at least one optical system (14) and at least one image acquisition sensor system (16) coupled to the optical system (14), which are configured to generate image data of an object region (18) that comprise spatial and spectral information;

an image analysis unit (20) that is configured to create an analysis of the image data that is based on spatial and spectral information, wherein the analysis comprises at least one evaluation which comprises at least one evaluation parameter which relates to an object subregion (22) of the object region (18);

an assessment unit (24) which is configured to generate an assessment, based on the analysis and on the basis of information relating to a diagnostic and/or therapeutic activity that is to be carried out and/or has been carried out, of an attribute of the object subregion (22) relevant to the diagnostic and/or therapeutic activity, which assessment is based on the evaluation parameter; and an output generating unit (26) that is configured to generate an output based on the assessment.

Aspect 2. Medical imaging device (10) according to aspect 1, further comprising a recommendation unit (28) that is configured to generate a recommendation for a user based on the assessment of the attribute of the object subregion (22), wherein the output generation unit (26) is configured to generate the output based on the recommendation.

Aspect 3. Medical imaging device (10) according to aspect 2, wherein the recommendation is a recommended action for carrying out a diagnostic and/or therapeutic activity on a patient.

Aspect 4. Medical imaging device (10) according to aspect 2 or 3, wherein the recommendation concerns the selection, and/or setting, and/or handling of a medical device (30) different from the imaging device (10).

Aspect 5. Medical imaging device (10) according to any of aspects 2 to 4, wherein the recommendation relates to whether and/or in which region the object region (18) should be surgically engaged, and/or wherein the recommendation relates to whether and/or in which region the object region (18) should not be surgically engaged.

Aspect 6. Medical imaging device (10) according to any of aspects 2 to 5, wherein the recommendation is based on a comparison of the assessment with a database (32) that contains data records on different diagnostic and/or therapeutic activities which are to be carried out and/or have been carried out as well as associated recommendations.

Aspect 7. Medical imaging device (10) according to any of aspects 2 to 6, wherein the assessment comprises a detection and/or classification of risk structures (34, 36), and wherein the recommendation comprises information regarding the detection and/or classification of risk structures (34, 36).

Aspect 8. Medical imaging device (10) according to any of aspects 2 to 7, further comprising an evaluation unit (38) that is configured to assign at least one evaluation to the recommendation in response to a behavior of the user caused by the recommendation.

Aspect 9. Medical imaging device (10) according to aspect 8, wherein the evaluation unit (38) is configured to transmit the evaluation to a recommendation database (40).

Aspect 10. Medical imaging device (10) according to any of aspects 2 to 9, wherein the image acquisition unit (12) is configured to generate continuously updated image data, and wherein the recommendation unit (28) is configured to adapt the recommendation substantially in real time depending on continuously updated image data.

Aspect 11. Medical imaging device (10) according to any of the preceding aspects, further comprising a parameter determination unit (42) which is configured to determine at least one control parameter for controlling a medical device (30) on the basis of the assessment of the attribute of the object subregion (22), wherein the output generation unit (26) is configured to generate the output based on the at least one control parameter.

Aspect 12. Medical imaging device (10) according to aspect 11, further comprising a device interface (44) which is connectable to a medical device (30) and which is configured to transmit the at least one control parameter to the medical device (30).

Aspect 13. Medical imaging device (10) according to aspect 11 or 12, wherein the output comprises a suggestion for a user to automatically pass on the at least one control parameter to a medical device (30) that is controllable by means of the control parameter.

Aspect 14. Medical imaging device (10) according to aspect 13, further comprising a user interface (46) configured to receive at least one user input by means of which the user can accept and/or reject and/or adapt the suggestion.

Aspect 15. Medical imaging device (10) according to any of aspects 11 to 14, wherein the image acquisition unit (12) is configured to generate continuously updated image data, and wherein the parameter determination unit (42) is configured to adapt the at least one control parameter substantially in real time depending on continuously updated image data.

Aspect 16. Medical imaging device (10) according to any of aspects 11 to 15, wherein the at least one control parameter is configured to determine an operating mode of the medical device (30).

Aspect 17. Medical imaging device according to any of aspects 11 to 16, wherein the at least one control parameter is configured to cause a safety-relevant shutdown of the medical device (30).

Aspect 18. Medical imaging device (10) according to any of the preceding aspects, wherein the assessment comprises an evaluation of the quality of a diagnostic examination and/or a treatment outcome, and wherein the output comprises information regarding the quality of the diagnostic examination and/or the treatment outcome.

Aspect 19. Medical imaging device (10) according to any of the preceding aspects,
wherein the assessment is based on at least two different sets of image data and comprises a comparison of the attribute of the object subregion at two different points in time.

Aspect 20. Medical imaging device (10) according to any of the preceding aspects,
wherein the analysis of the image data comprises image segmentation.

Aspect 21. Medical imaging device (10) according to any of the preceding aspects,
wherein the analysis of the image data comprises tissue detection.

Aspect 22. Medical imaging device according to any of the preceding aspects,
wherein the analysis of the image data comprises the detection of at least one medical device (30).

Aspect 23. Medical imaging device (10) according to aspect 22,
wherein the detection of the at least one medical device (30) comprises information about a type, and/or an orientation, and/or a position, and/or a state of the medical device (30).

Aspect 24. Medical imaging device (10) according to any of the preceding aspects,
wherein the attribute comprises information about anatomical and/or physiological features of the object subregion (22).

Aspect 25. Medical imaging device (10) according to any of the preceding aspects,
further comprising a smoke detection unit (48) and/or a contamination detection unit (50) which is configured to detect a presence and/or absence of smoke and/or contamination in the object region (18) and/or on a window (52).

Aspect 26. Medical imaging device (10) according to aspect 25,
wherein the assessment unit is configured to take into account the presence and/or absence of smoke and/or contamination in the object region (18) and/or on the window (52) detected by the smoke detection unit (48) and/or the contamination detection unit (50) in the assessment of the attribute.

Aspect 27. Medical imaging device (10) according to aspect 25 or 26,
wherein the image acquisition unit (12) is configured to regenerate image data of the object region (18) at a time after the generation of the image data of the object region (18) when the smoke detection unit (48) has detected the presence of smoke in the object region (18) based on the image data of the object region (18).

Aspect 28. Medical imaging device (10) according to any of the preceding aspects,
wherein the output comprises at least one overlay (54) directed to a user, which is superimposed on a pictorial representation of the object region (18).

Aspect 29. Medical imaging device (10) according to aspect 28,
wherein the overlay (54) comprises a highlighting and/or coloring at least of regions of a pictorial representation of the object region (18).

Aspect 30. Medical imaging device (10) according to any of the preceding aspects,
wherein the output comprises at least one audio output directed to a user.

Aspect 31. Medical imaging device (10) according to any of the preceding aspects,
wherein the output concerns a classification of tissue.

Aspect 32. Medical imaging device (10) according to any of the preceding aspects,
wherein the output comprises a suitability and/or unsuitability of at least one object subregion (22) of the object region (18) for the diagnostic and/or therapeutic activity to be carried out.

Aspect 33. Medical imaging device (10) according to any of the preceding aspects,
wherein the output concerns the quality of a result of the performed diagnostic and/or therapeutic activity.

Aspect 34. Medical imaging device (10) according to any of the preceding aspects,
wherein the output comprises a warning directed to a user.

Aspect 35. Medical imaging device (10) according to any of the preceding aspects,
wherein the analysis comprises a comparison of normalized and/or standardized spectral data.

Aspect 36. Medical imaging device (10) according to any of the preceding aspects,
wherein the analysis comprises a comparison of spectral data for different spectral ranges.

Aspect 37. Medical imaging device (10) according to any of the preceding aspects,
wherein the optical system (14) and the image acquisition sensor system (16) of the image acquisition unit (12) are configured to acquire hyperspectral image data.

Aspect 38. Medical imaging device (10) according to any of the preceding aspects,
wherein the spectral information concerns the absorption of light.

Aspect 39. Medical imaging device according to any of the preceding aspects,
wherein the analysis comprises an assignment of the image data to three-dimensional data that relate to the object region (18).

Aspect 40. Medical imaging device (10) according to any of the preceding aspects,
wherein the diagnostic and/or therapeutic activity that is to be carried out and/or has been carried out comprises an energy input into tissue, in particular a thermal and/or electrosurgical and/or radiation-based energy input.

Aspect 41. Medical imaging device (10) according to any of the preceding aspects,
wherein the evaluation parameter contains information regarding tissue coagulation, in particular regarding vessel sealing, tube sterilization and/or the welding and/or connection of tissue structures, such as the formation of anastomoses.

Aspect 42. Medical imaging device (10) according to any of the preceding aspects,
wherein the image acquisition unit (12) is multimodal and can be operated in at least a first mode in which spatially and spectrally resolved image data can be generated, and in at least a second mode in which only spatially resolved image data can be generated.

Aspect 43. Medical imaging device (10) according to any of the preceding aspects,
wherein the diagnostic and/or therapeutic activity that is to be performed and/or has been performed is real and/or virtual.

Aspect 44. Medical imaging device (10) according to any of the preceding aspects, wherein the assessment is additionally based on patient-specific data that are different from the image data.

Aspect 45. Medical imaging device (10) according to any of the preceding aspects, wherein the image acquisition unit (12) is stereoscopic.

Aspect 46. Medical system (56), comprising:

a medical imaging device (10) according to any of the preceding aspects; and a medical device (30).

Aspect 47. Medical system (56) according to aspect 46, wherein the medical imaging device (10) comprises a device interface (44), and wherein the medical device (30) is connectable and/or connected to the device interface (44) of the imaging device (10).

Aspect 48. Medical system (56) according to aspect 46 or 47, wherein the medical device (30) is a tissue-coagulating, in particular vessel-sealing or tissue-fusing, instrument.

Aspect 49. Method for operating a medical imaging device (10), in particular a medical imaging device (10) according to any of aspects 1 to 45, wherein the medical imaging device (10) comprises a spatially and spectrally resolving image acquisition unit (12) which comprises at least one optical system (14) and at least one image acquisition sensor system (16) coupled to the optical system (14), which are configured to generate image data of an object region (18) that comprise spatial and spectral information, comprising the steps of:

at least partially automated creation of an analysis of the image data, which is based on spatial and spectral information, wherein the analysis comprises at least one evaluation which comprises at least one evaluation parameter which relates to an object subregion (22) of an object region (18);

at least partially automated generation, based on the analysis and on the basis of information relating to a diagnostic and/or therapeutic activity that is to be carried out and/or has been carried out, of an assessment of an attribute of the object subregion (22) relevant to the diagnostic and/or therapeutic activity, which assessment is based on the evaluation parameter; and at least partially automated output of an output that is based on the assessment.

Aspect 50. Method for medical imaging, in particular carried out with a medical imaging device (10) according to any of aspects 1 to 45 and/or with a medical system (56) according to any of aspects 46 to 48, comprising the steps of:

at least partially automated generation of image data of an object region (18) that comprises spatial and spectral information;

at least partially automated creation of an analysis of the image data, which is based on spatial and spectral information, wherein the analysis comprises at least one evaluation which comprises at least one evaluation parameter which relates to an object subregion (22) of an object region (18);

at least partially automated generation, based on the analysis and on the basis of information relating to a diagnostic and/or therapeutic activity that is to be carried out and/or has been carried out, of an assessment of an attribute of the object subregion (22) relevant to the diagnostic and/or therapeutic activity, which assessment is based on the evaluation parameter; and at least partially automated output of an output that is based on the assessment.

Aspect 51. Control unit comprising a processor and a memory, wherein program code is saved on the memory which, when it is executed by the processor, causes a method according to aspect 49 or 50 to be carried out.

Aspect 52. Program code which, when it is executed by a processor and/or a control unit and/or a computer, is configured to cause a method according to aspect 49 or 50 to be carried out.

Aspect 53. Computer program product comprising a computer-readable medium and program code according to aspect 52 saved on the computer-readable medium.

LIST OF REFERENCE SIGNS

10 Medical imaging device
11 Control unit
12 Image acquisition unit
14 Optical system
16 Image acquisition sensor system
18 Object region
20 Image analysis unit
22 Object subregion
24 Assessment unit
26 Output generation unit
28 Recommendation unit
30 Medical device
32 Database
34 Risk structure
36 Risk structure
38 Evaluation unit
40 Recommendation database
42 Parameter determination unit
44 Device interface
46 User interface
48 Smoke detection unit
50 Contamination detection unit
52 Window
54 Overlay
56 Medical system
58 Medical imaging unit
60 Lighting device
62 Control unit
66 Distal portion
68 Proximal portion
70 Handle
72 Display device
74 Output unit
76 Loudspeaker
78 Display
80 Structure
82 Structure
84 Vessel
86 Surgical robot

The invention claimed is:

1. A medical imaging device comprising:

a spatially and spectrally resolving image acquisition unit which comprises at least one optical system and at least one image acquisition sensor system coupled to the optical system, which are configured to generate image data of an object region that comprisecomprises spatial and spectral information, wherein the image acquisition unit is configured for at least one of multispectral and hyperspectral image acquisition, and the image data includes one or more of multispectral and hyperspectral image data;

an image analysis unit that is configured to automatically and in real-time or near-real time create an analysis of the image data that is based at least on the spatial and spectral information, wherein the analysis comprises at least one evaluation which comprises at least one evaluation parameter which relates to an object subregion of the object region, and the image analysis unit is further configured to use selected spectral ranges for performing an image segmentation to assist with the at least one evaluation;

an assessment unit which is configured to automatically generate, based on the analysis and on the basis of information relating to a diagnostic and/or therapeutic activity that is to be carried out and/or has been carried out, an assessment of an attribute of the object subregion relevant to the diagnostic and/or therapeutic activity, which assessment is based on the evaluation parameter; and an output generating unit that is configured to generate and transmit an output based on the assessment, the output being at least one control parameter that is configured to control an operating mode of a medical device, wherein the assessment is adapted in real-time or near real-time based on continuously updated image data.

2. The medical imaging device according to claim 1, further comprising a parameter determination unit which is configured to determine the at least one control parameter for controlling the medical device on the basis of the assessment of the attribute of the object subregion, the control parameter being determined by a machine learning algorithm.

3. The medical imaging device according to claim 2, further comprising a device interface which is connectable to thea medical device and which is configured to transmit the at least one control parameter to the medical device; and/or wherein the output comprises a suggestion for a user to automatically pass on the at least one control parameter to a medical device that is controllable by means ofthe control parameter.

4. The medical imaging device according to claim 3, further comprising a user interface configured to receive at least one user input by which the user can accept and/or reject and/or adapt the suggestion.

5. The medical imaging device according to claim 2, wherein the image acquisition unit is configured to generate continuously updated image data, and wherein the parameter determination unit is configured to adapt the at least one control parameter substantially in real-time depending on continuously updated image data.

6. The medical imaging device according to claim 2, wherein the at least one control parameter is configured to specify the operating mode of the medical device; and/or wherein the at least one control parameter is configured to cause a safety-relevant shutdown of the medical device.

7. The medical imaging device according to claim 1, further comprising a smoke detection unit and/or a contamination detection unit which is configured to detect a presence and/or absence of smoke and/or contamination in the object region and/or on a window.

8. The medical imaging device according to claim 7, wherein the assessment unit is configured to take into account the presence and/or absence of smoke and/or contamination in the object region and/or on the window detected by the smoke detection unit and/or the contamination detection unit in the assessment of the attribute; and/or wherein the image acquisition unit is configured to regenerate image data of the object region at a time after the generation of the image data of the object region when the smoke detection unit has detected the presence of smoke in the object region based on the image data of the object region.

9. The medical imaging device according to claim 1, wherein the analysis comprises a comparison of normalized and/or standardized spectral data; and/or wherein the analysis comprises a comparison of spectral data for different spectral ranges.

10. The medical imaging device according to claim 1, wherein the optical system and the image acquisition sensor system of the image acquisition unit are configured to acquire hyperspectral image data; and/or wherein the spectral information relates to the absorption of light; and/or wherein the image acquisition unit is multimodal and can be operated in at least a first mode in which spatially and spectrally resolved image data can be generated, and in at least a second mode in which only spatially resolved image data can be generated.

11. A medical system, comprising:
the medical imaging device according to claim 1, and the medical device.

12. A method to operate a medical imaging device that includes a spatially and spectrally resolving image acquisition unit which comprises at least one optical system and at least one image acquisition sensor system coupled to the optical system, which are configured to generate image data of an object region that comprise spatial and spectral information, comprising:

at least partially automated creation of an analysis of the image data in real-time or near real-time, which is based on spatial and spectral information, wherein the image data includes one or more of multispectral and hyperspectral image data, wherein the analysis comprises at least one evaluation which comprises at least one evaluation parameter which relates to an object subregion of an object region, and wherein selected spectral ranges are used for performing an image segmentation to assist with the at least one evaluation;

at least partially automated generation, based on the analysis and on the basis of information relating to a diagnostic and/or therapeutic activity that is to be carried out and/or has been carried out, of an assessment of an attribute of the object subregion relevant to the diagnostic and/or therapeutic activity, which assessment is based on the evaluation parameter; and at least partially automated output and transmission of an output that is based on the assessment, the output being at least one control parameter that is configured to control an operating mode of a medical device, wherein the assessment is adapted in real-time or near real-time based on continuously updated image data.

13. The method for medical imaging comprising:
at least partially automated generation of image data of an object region that comprises spatial and spectral information, wherein the image data includes one or more of multispectral and hyperspectral image data;

at least partially automated creation of an analysis of the image data, which is based on spatial and spectral information, wherein selected spectral ranges are used for performing an image segmentation to assist with the at least one evaluation, and wherein the analysis comprises at least one evaluation which comprises at least one evaluation parameter which relates to an object subregion of an object region, wherein one or more selected spectral ranges are used for performing an image segmentation to assist with the at least one evaluation;

at least partially automated generation, based on the analysis and on the basis of information relating to a diagnostic and/or therapeutic activity that is to be carried out and/or has been carried out, of an assessment of an attribute of the object subregion relevant to the diagnostic and/or therapeutic activity, which assessment is based on the evaluation parameter; and at least partially automated output of an output that is based on the assessment, the output being at least one control parameter that is configured to control an operating mode of a medical device, wherein the assessment is adapted in real-time or near real-time based on continuously updated image data.

14. A non-transitory computer-readable information storage media having stored thereon instructions, that when executed by one or more processors, cause a method to be performed including:

at least partially automated creation of an analysis of the image data in real-time or near real-time, which is based on spatial and spectral information, wherein the image data includes one or more of multispectral and hyperspectral image data, wherein the analysis comprises at least one evaluation which comprises at least one evaluation parameter which relates to an object subregion of an object region, and wherein selected spectral ranges are used for performing an image segmentation to assist with the at least one evaluation;

at least partially automated generation, based on the analysis and on the basis of information relating to a diagnostic and/or therapeutic activity that is to be carried out and/or has been carried out, of an assessment of an attribute of the object subregion relevant to the diagnostic and/or therapeutic activity, which assessment is based on the evaluation parameter; and at least partially automated output and transmission of an output that is based on the assessment, the output being at least one control parameter that is configured to control an operating mode of a medical device, wherein the assessment is adapted in real-time or near real-time based on continuously updated image data.

15. A non-transitory computer-readable information storage media having stored thereon instructions, that when executed by one or more processors, cause a method to be performed including:

at least partially automated generation of image data of an object region that comprises spatial and spectral information, wherein the image data includes one or more of multispectral and hyperspectral image data;

at least partially automated creation of an analysis of the image data, which is based on spatial and spectral information, wherein selected spectral ranges are used for performing an image segmentation to assist with the at least one evaluation, and wherein the analysis comprises at least one evaluation which comprises at least one evaluation parameter which relates to an object subregion of an object region, wherein one or more selected spectral ranges are used for performing an image segmentation to assist with the at least one evaluation;

at least partially automated generation, based on the analysis and on the basis of information relating to a diagnostic and/or therapeutic activity that is to be carried out and/or has been carried out, of an assessment of an attribute of the object subregion relevant to the diagnostic and/or therapeutic activity, which assessment is based on the evaluation parameter; and at least partially automated output of an output that is based on the assessment, the output being at least one control parameter that is configured to control an operating mode of a medical device, wherein the assessment is adapted in real-time or near real-time based on continuously updated image data.

* * * * *